(12) United States Patent
Pouchoulin

(10) Patent No.: US 11,951,240 B2
(45) Date of Patent: Apr. 9, 2024

(54) APPARATUS FOR EXTRACORPOREAL BLOOD TREATMENT

(71) Applicant: GAMBRO LUNDIA AB, Lund (SE)

(72) Inventor: Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 17/785,192

(22) PCT Filed: Dec. 23, 2020

(86) PCT No.: PCT/IB2020/062407
§ 371 (c)(1),
(2) Date: Jun. 14, 2022

(87) PCT Pub. No.: WO2021/130701
PCT Pub. Date: Jul. 1, 2021

(65) Prior Publication Data
US 2023/0017204 A1    Jan. 19, 2023

(30) Foreign Application Priority Data

Dec. 23, 2019  (EP) ..................................... 19219245

(51) Int. Cl.
*A61M 1/16*      (2006.01)
*A61M 1/34*      (2006.01)

(52) U.S. Cl.
CPC ........ *A61M 1/1611* (2014.02); *A61M 1/3441* (2013.01)

(58) Field of Classification Search
CPC .. A61M 1/1611; A61M 1/3441; A61M 1/341; A61M 1/3431; A61M 1/3437; A61M 1/3458; A61M 2205/3331; A61M 2205/3334; A61M 2205/3393;
(Continued)

(56) References Cited

U.S. PATENT DOCUMENTS 5,578,223 A    11/1996  Bene
8,211,048 B2   7/2012   Szamosfalvi

OTHER PUBLICATIONS

Desai, Indian J Nephrol. Jul.-Aug. 2015;25(4): 189-193. (Year: 2015).*

(Continued)

*Primary Examiner* — Krishnan S Menon
(74) *Attorney, Agent, or Firm* — Mueting Raasch Group

(57) ABSTRACT

A CRRT apparatus comprising a filtration unit (2), a blood circuit (17), a blood pump (21), a dialysate line (13) and one or more lines (8; 51; 57; 58; 63; 69; 67; 74) to transfer a respective solution into blood; a fluid source for each of said one or more lines, wherein said solution comprises at least one buffer agent in the form of bicarbonate or bicarbonate precursor. A control unit (12) is configured to receive a patient prescription and to determine a parameter ($J_{buffer\_load}/BW$) indicative of a steady state acid-base balance in the blood of the patient who has to undergo a CRRT blood treatment, wherein said parameter is determined as a function of the concentration of said buffer agent in said fluid source and as a function of the estimated or calculated patient systemic steady state concentration of bicarbonate and/or bicarbonate precursors.

33 Claims, 2 Drawing Sheets

(58) Field of Classification Search
CPC .............. A61M 1/3609; A61M 1/3675; A61M 1/3672; A61M 1/36224; A61M 1/36225
See application file for complete search history.

(56) References Cited

OTHER PUBLICATIONS

PCT Search Report and Written Opinion for PCT/IB2020/062407 dated Mar. 17, 2021 (13 pages).
Extended European Search Report for Application No. 1219245.8 dated Jul. 2, 2020 (8 pages).

* cited by examiner

APPARATUS FOR EXTRACORPOREAL BLOOD TREATMENT

This application is a U.S. National Stage Application of International Application No. PCT/IB2020/062407 filed Dec. 23, 2020, which was published in English on Jul. 1, 2021 as International Publication No. WO 2021/130701 A1. International Application No. PCT/IB2020/062407 claims priority to European Application No. 19219245.8 filed Dec. 23, 2019.

TECHNICAL FIELD

The present invention relates to an apparatus for extracorporeal blood treatment and a method for controlling the extracorporeal blood treatment apparatus. In more detail, the present invention is applicable in the context of continuous renal replacement therapies (CRRT) with or without anticoagulation, for example CRRT with or without systemic anticoagulation (e.g., heparin)/with or without regional anticoagulation (e.g., citrate).

In particular, the present invention may be advantageously used for administering regional citrate anticoagulation (RCA) during continuous renal replacement therapies (CRRT). Furthermore, the apparatus of the present invention may be also advantageously used in CRRT therapies for efficiently remove $CO_2$ with use of extracorporeal $CO_2$ removal, or $ECCO_2R$, via extracorporeal blood circulation as an alternative or supplement to mechanical ventilation.

BACKGROUND OF THE INVENTION

The kidneys fulfil many functions, including the removal of water, the excretion of catabolites (or waste from the metabolism, for example urea and creatinine), the regulation of the concentration of the electrolytes in the blood (e.g. sodium, potassium, magnesium, calcium, bicarbonates, phosphates, chlorides) and the regulation of the acid/base equilibrium within the body, which is obtained in particular by the removal of weak acids and by the production of ammonium salts. In individuals who have lost (temporarily or permanently) the use of their kidneys, since these excretion and regulation mechanisms no longer work, the body accumulates water and waste from the metabolism and exhibits an excess of electrolytes, as well as, in general, acidosis, the pH of the blood plasma shifting downwards, below 7.35 (the blood pH normally varies within narrow limits of between 7.35 and 7.45). As mentioned, in order to overcome renal dysfunction, resort is conventionally made to a blood treatment involving extracorporeal circulation through an exchanger having a semipermeable membrane (dialyzer) in which the patients blood is circulated on one side of the membrane and a dialysis liquid, comprising the main electrolytes of the blood in concentrations close to those in the blood of a healthy subject, is circulated on the other side. Furthermore, a pressure difference is created between the two compartments of the dialyzer which are delimited by the semipermeable membrane, so that a fraction of the plasma fluid passes by ultrafiltration through the membrane into the compartment containing the dialysis liquid. The blood treatment which takes place in a dialyzer as regards waste from the metabolism and electrolytes results from two mechanisms of molecular transport through the membrane. On the one hand, the molecules migrate from the liquid where their concentration is higher to the liquid where their concentration is lower. This is diffusive transport. On the other hand, certain catabolites and certain electrolytes are entrained by the plasma fluid which filters through the membrane under the effect of the pressure difference created between the two compartments of the exchanger. This is convective transport. Three of the above-mentioned functions of the kidney, namely the removal of water, the excretion of catabolites and the regulation of the electrolytic concentration of the blood, are therefore performed in a conventional blood treatment device by the combination of dialysis and blood filtration (this combination is referred to as hemodiafiltration). As regards the regulation of the acid/base equilibrium inside the body, the approach adopted to overcome renal deficiency is to act on a mechanism by which the acid/base equilibrium inside the body is regulated, this mechanism consisting of the buffer systems of the blood, the main one of which comprises carbonic acid, as a weak acid, associated with its alkali salt, bicarbonate. This is why, in order to correct acidosis in a patient suffering from renal insufficiency, he/she is administered with bicarbonate via the vascular route, directly or indirectly, during a hemodialysis session. In the field of renal treatment, continuous renal replacement therapy (CRRT) has been widely used in critically ill patients with acute kidney injury and anticoagulation of the extracorporeal blood is necessary to maintain the patency of the circuit. In recent decades, different anticoagulation strategies have been used in clinical settings and heparin is the most commonly used anticoagulant. Although heparin has the advantages of low cost, easy monitoring and simple reversal, it may increase bleeding. Additionally, there is the risk of heparin-induced thrombocytopenia type II that can result in life-threatening complications. Regional citrate anticoagulation (RCA), which was first introduced into clinical use in the early 1980s, has been recommended as the most suitable form of CRRT regional circuit anticoagulation and has been safely used even in patients with severe liver dysfunction. However, citrate infusion in critically ill patients impacts a variety of metabolic systems, which can lead to metabolic alkalosis, hypocalcaemia and citrate excessive load/toxicity. These potential disturbances may be partially resolved by careful monitoring, adherence to treatment protocols, and oversight by trained staff in clinical practice. Notwithstanding the above criticalities, citrate anticoagulation has become the preferred anticoagulation choice for continuous renal replacement therapies (CRRT) as minimizing patient bleeding risks (regional anticoagulation effect) and increasing extracorporeal blood circuit life time. While RCA has some limitations with respect to compatibility with 'large' blood flow rates, this is not a problem in CRRT where efficiency is primarily driven by the fluid exchange rate and where the vast majority of treatments are delivered at blood flow rate below 200 ml/min. On the other hand, efficiency of $ECCO_2R$ therapy is more or less proportional to blood flow rate and blood flows in the 350-450 ml/min range are typically prescribed. These large blood flow rates are clearly incompatible with the typical RCA prescription used in CRRT (citrate dose of 3.0 mmol/L of blood) due to high amounts of citrate infused to the patients (citrate load) and associated effects. The effects of high patient citrate load includes metabolic alkalosis and citrate accumulation/hypocalcemia. Fast metabolism of the citrate infused to the patient is part of the key mechanisms making RCA successful. Citrate metabolism produces energy, as well as bicarbonate and $CO_2$ while releasing complexed calcium. In the situation where large amounts of citrate are infused to the patient, large amounts of bicarbonate are produced, up to the point where metabolic alkalosis is generated. Citrate accumulation matches with the scenario where systemic citrate concentration is significantly increased. It can develop in two circumstances 'normal' citrate load combined to poor citrate metabolism, and 'normal' citrate metabolism combined to large citrate load. The first scenario is likely to lead to metabolic acidosis due to a low production rate of bicarbonate from citrate. The second scenario is to be considered, specifically in respect to CRRT therapies in the ECCO$_2$R-RCA context. Consequence of citrate accumulation is a need to increase total calcium concentration as to keep (systemic) ionised calcium within the physiological range. This can be achieved by increasing the calcium infusion rate. This problem is a transitory problem during initiation of the therapy, as a safe steady state can be reached after stabilization of systemic citrate concentration (6-8 hours). Discontinuation of the therapy may however lead to an episode of hypercalcemia (as citrate is metabolized and complex-bound calcium is released). In the clinical setting, citrate accumulation is diagnosed via the monitoring of total to ionised systemic calcium ratio (ratio>2.5 indicating probable citrate accumulation). Therefore, though regional anticoagulation may highly alleviate the adverse effects of heparin, RCA imposes the need of proper monitoring the acid-base balance in the patient blood, severely increasing the risk of alkalosis. Further, in ECCO$_2$R treatments, RCA cannot be implemented satisfactorily due to contradictory requirements of ECCO$_2$R and RCA modalities:

in ECCO$_2$R, CO$_2$ removal performance is directly related to blood flow rate with removal rate increasing strongly with blood flow;

in the current CRRT operating conditions with moderate fluid exchange rate (about 30 ml/kg/h), high blood flow rates are not possible as leading to excessive citrate infusion to the patient (via the returned blood) which may lead to both metabolic alkalosis and hypocalcemia. Thus, current designs of ECCO$_2$R and RCA-CRRT drive contradictory requirements on blood flow rate making impossible delivery of satisfactory CO$_2$ removal (removal>50 ml/min), when CRRT with RCA can hardly be safely performed at blood flow rates beyond 200 ml/min in available commercial CRRT systems.

EP0678301 relates to an artificial kidney for intensive care particularly adapted to treating people suffering temporarily from kidney failure following an accident or a surgical operation. As clarified in the prior art document, in addition to purifying plasma wastes (e.g. urea) and to remove excess water, the kidneys play an important role in maintaining the acid-base equilibrium of the blood. Since the final concentration of bicarbonate in the blood depends on the concentration of bicarbonate in the perfusion solution or in the dialysis liquid, on the respective flow rates thereof, and on the flow rate of the patients blood through the membrane exchanger, the main problem at the basis of document EP0678301 is that the concentration of bicarbonate in the blood of the patient corresponds rarely exactly to the desired concentration. EP0678301 describes a blood treatment device including a dialyzer with two chambers separated by a membrane. A dialysis liquid container (that does not contain any bicarbonate) is connected to a fluid pump via a duct which runs to the second chamber of the dialyzer. Electromagnetic clamps are provided for connecting the container to either the dialyzer or to the blood circuit. A bubble trap is provided in the return line of the blood circuit. The bubble trap is linked to an infusion container containing a solution of bicarbonate. In accordance with EP0678301, the flow rate QHCO3 of the circulation pump is controlled as a function of the flow rate QOUT of the dialysate pump regardless of the type of treatment being delivered to the patient either by the equation:

$$Q_{HCO3}=Q_{OUT}*[HCO_3]_{DES}/[HCO_3]_{SOL}$$

or by the equation:

$$Q_{HCO3}=Cl*[HCO_3]_{DES}/[HCO_3]_{SOL}$$

wherein:

$Q_{HCO3}$ is flow rate of the circulation pump;

$Q_{OUT}$ is the flow rate $Q_{OUT}$ of the dialysate pump;

$[HCO_3]_{DES}$ is the desired concentration of bicarbonate in the blood of the patient;

$[HCO_3]_{SOL}$ is the concentration of the solution in the container,

Cl is the clearance of the dialyzer for bicarbonate.

Notably, this prior art is directed to proper adjustment of patient blood acid-base equilibrium, by using a specific control of post infusion of bicarbonate solution based on clearance/dialysate flow rate which exclusively works in the following dialysis machine configurations: HF with post dilution and HD(F) with post dilution. Therefore, the problem of proper acid-base management in configuration wherein citrate is infused pre-blood pump (e.g., regional anticoagulation systems) and/or bicarbonate containing solution is pre-infused remains unsolved.

As to adapting to specific patient condition, protocols may (by far not systematically) include guidelines for adjusting citrate infusion or dialysis fluid/replacement flow rates in case patient monitoring data evidence alkalosis or acidosis problems. When present, these guidelines appear largely empirical. In the case of acidosis, some literature report for the infusion of bicarbonate 'bolus'. Although some published protocols are derived from some upstream modelling, no parameter representative of the expected buffer balance from the therapy is made explicitly available, whatever 'original' protocol parameters are used or after these have been tuned further to patient monitoring data.

SUMMARY

An aim of the present invention is providing an extracorporeal blood treatment apparatus able to alleviate or fix at least one of the prior art drawbacks.

In detail it is an aim of the present embodiments to allow for acid-balance control/management, wherein the system is also designed to vary buffer balance of the extracorporeal blood circuit in an easy and controlled way.

A further goal is to increase safety of RCA prescriptions by alerting operator in the case of prescription at significant risk of patient alkalosis or acidosis, in particular in the ICU context where prescriber may not be an expert in dialysis, and/or starting with RCA.

Some embodiments make easier/safer RCA prescription for patients of 'unusual' size for whom standard prescription may not be adapted.

A further aim of some of the described embodiments is to provide an extracorporeal blood treatment apparatus configured to safely allow CRRT+ECCO$_2$R treatments and/or extracorporeal blood treatments using regional anticoagulation during CRRT therapies, namely to make available a dialysis apparatus able to provide ECCO$_2$R treatments and CRRT treatments using regional anticoagulation, in particular RCA.

An auxiliary goal is to make available an extracorporeal blood treatment apparatus configured to keep the buffer balance within acceptable ranges even in configurations operating the system with large blood flow rate.

At least one of the above-indicated aims is attained by an apparatus and a corresponding method as in one or more of the appended claims, taken singly or in any combination.

According to a first independent aspect of the invention an extracorporeal blood treatment device, in particular a continuous renal replacement therapy (CRRT) apparatus, is provided comprising:
- a filtration unit (2) having a primary chamber and a secondary chamber separated by a semi-permeable membrane;
- a blood circuit (17) having a blood withdrawal line (6) connected to an inlet of the primary chamber (3), and a blood return line (7) connected to an outlet of the primary chamber (3), said blood circuit being configured for connection to a patient cardiovascular system;
- a blood pump (21) to circulate blood in the blood circuit (17);
- a dialysate line (13) connected to an outlet of the secondary chamber (4);
- one or more lines (8; 51; 58; 63; 74) for infusing a respective solution into blood;
- at least one fluid source of a solution for each of said one or more lines, wherein said solution comprises at least one buffer agent in the form of bicarbonate or bicarbonate precursor,
- a control unit (12) configured to receive a patient prescription including parameters for setting a CRRT blood treatment, characterized in that the control unit (12) is further configured to either.
- determine a parameter ($J_{buffer\_load}$/BW) indicative of a steady state acid-base balance in the blood of the patient who has to undergo the CRRT blood treatment, wherein said parameter is determined as a function of the concentration of said buffer agent in said fluid source and as a function of the estimated or calculated patient systemic steady state concentration of bicarbonate and/or bicarbonate precursors; or
- determine a parameter ($Cp_{HCO3\_pat}$) indicative of a steady state bicarbonate concentration in the blood of the patient who has to undergo the CRRT blood treatment, wherein said parameter is determined as a function of the concentration of said buffer agent in said fluid source and as a function of an estimated or calculated net buffer load ($J_{buffer\_load}$/BW) indicative of a steady state acid-base balance in the blood of the patient.

In a further independent aspect, a method of determining a parameter ($J_{buffer\_load}$/BW) indicative of a steady state acid-base balance in the blood of the patient who has to undergo the CRRT blood treatment is provided, the method being for an extracorporeal blood treatment device, in particular a continuous renal replacement therapy (CRRT) apparatus, comprising:
- a filtration unit (2) having a primary chamber (3) and a secondary chamber (4) separated by a semi-permeable membrane (5);
- a blood circuit (17) having a blood withdrawal line (6) connected to an inlet of the primary chamber (3), and a blood return line (7) connected to an outlet of the primary chamber (3), said blood circuit being configured for connection to a patient cardiovascular system;
- a blood pump (21) to circulate blood in the blood circuit (17);
- a dialysate line (13) connected to an outlet of the secondary chamber (4);
- one or more lines (8; 51; 58; 63; 74) for infusing a respective solution into blood;
- at least one fluid source of a solution for each of said one or more lines, wherein said solution comprises at least one buffer agent in the form of bicarbonate or bicarbonate precursor,
- a control unit (12), the method comprising the following steps: receiving a patient prescription including parameters for setting a CRRT blood treatment, determining a parameter ($J_{buffer\_load}$/BW) indicative of a steady state acid-base balance in the blood of the patient who has to undergo the CRRT blood treatment, wherein said parameter is determined as a function of the concentration of said buffer agent in said fluid source and as a function of the estimated or calculated patient systemic steady state concentration of bicarbonate and/or bicarbonate precursors, wherein the steps are carried out by the control unit.

In a further independent aspect, a method of determining a parameter ($Cp_{HCO3\_pat}$) indicative of a steady state bicarbonate concentration in the blood of the patient who has to undergo the CRRT blood treatment is provided, the method being for an extracorporeal blood treatment device, in particular a continuous renal replacement therapy (CRRT) apparatus, comprising:
- a filtration unit (2) having a primary chamber (3) and a secondary chamber (4) separated by a semi-permeable membrane (5);
- a blood circuit (17) having a blood withdrawal line (6) connected to an inlet of the primary chamber (3), and a blood return line (7) connected to an outlet of the primary chamber (3), said blood circuit being configured for connection to a patient cardiovascular system;
- a blood pump (21) to circulate blood in the blood circuit (17);
- a dialysate line (13) connected to an outlet of the secondary chamber (4);
- one or more lines (8; 51; 58; 63; 74) for infusing a respective solution into blood;
- at least one fluid source of a solution for each of said one or more lines, wherein said solution comprises at least one buffer agent in the form of bicarbonate or bicarbonate precursor,
- a control unit (12), the method comprising the following steps: receiving a patient prescription including parameters for setting a CRRT blood treatment, determining a parameter ($Cp_{HCO3\_pat}$) indicative of a steady state bicarbonate concentration in the blood of the patient who has to undergo the CRRT blood treatment, wherein said parameter is determined as a function of the concentration of said buffer agent in said fluid source and as a function of the estimated or calculated steady state acid-base balance in the blood of the patient, wherein the steps are carried out by the control unit.

In a $2^{nd}$ aspect according to any one of the previous aspects, the parameter ($J_{buffer\_load}$/BW) indicative of a steady state acid-base balance in the blood of the patient undergoing a CRRT treatment is a parameter function of a net buffer load (NBL) in the patient expected at a steady state, in particular a normalized net buffer (nNBL) load in the patient expected at a steady state, in more detail $$\frac{J_{buffer\_load}}{BW} = nNBL = \frac{NBL}{BW}.$$

In a 3$^{rd}$ aspect, according to the previous aspect, the net buffer load (NBL) is normalized over a patient body weight (BW).

In a 4$^{th}$ aspect according to any one of the previous aspects, the bicarbonate precursor includes citrate, lactate and/or acetate.

In a 5$^{th}$ aspect according to anyone of the previous aspects, said at least one fluid source of a solution comprises a solution bag connected to an end of the line for infusing a solution into blood.

In a 6$^{th}$ aspect according to anyone of the previous aspects, said one or more lines (8; 51; 58; 63; 74) for infusing a respective solution into blood comprises an infusion line (63) for infusing into the blood a substitute solution including bicarbonate or bicarbonate precursor, in particular for directly infusing the substitute solution into the blood circuit (17). Preferably the substitute solution includes bicarbonate.

In a 7$^{th}$ aspect according to anyone of the previous aspects, the apparatus comprises a replacement solution bag (64) connected to an end of an infusion line (63) for infusing a solution including bicarbonate into blood.

In an 8$^{th}$ aspect according to the previous two aspects, the infusion line (63) is connected to the blood return line (7) to post-infuse the solution including bicarbonate, in particular the infusion line (63) comprising a pre-infusion branch (67) and a post-infusion branch (69) to allow infusing both upstream and downstream the filtration unit (2).

In a 9$^{th}$ aspect according to any one of the previous three aspects, the infusion line (63) is connected to the blood withdrawal line (6) to pre-infuse the solution including bicarbonate, in particular the infusion line (63) comprising a pre-infusion branch (67) and a post-infusion branch (69) to allow infusing both upstream and downstream the filtration unit (2).

In a 10$^{th}$ aspect according to anyone of the previous four aspects, including an infusion pump (65) operating on the infusion line (63) to determine a replacement infusion rate ($Q_{rep}$).

In an 11$^{th}$ aspect according to anyone of the previous aspects, said one or more lines (8; 51; 58; 63; 74) for infusing a respective solution into blood comprises a supply line (8) for directly infusing into the blood circuit (17) a dialysis fluid including bicarbonate, in particular through an infusion branch (58).

In a 12$^{th}$ aspect according to the previous aspect, the apparatus comprises a dialysis liquid bag (64) connected to an end of the supply line (8) for infusing a solution including bicarbonate into the filtration unit (2) and/or into the blood circuit (17).

In a 13$^{th}$ aspect according to the previous two aspects, the infusion branch (58) is connected to the blood return line (7) to post-infuse the solution including bicarbonate, in particular the supply line (8) comprising an intake branch (57) to direct fluid to the second chamber of the filtration unit.

In a 14$^{th}$ aspect according to anyone of the previous three aspects, the apparatus includes a dialysis fluid pump (25) operating on the supply line (8) to determine a dialysis flow rate ($Q_d$).

In a 15$^{th}$ aspect according to anyone of the previous aspects, said one or more lines (8; 51; 58; 63; 74) for infusing a respective solution into blood comprises an ion replacement infusion line (74) for infusing into the blood an ion balancing solution including calcium.

In a 16$^{th}$ aspect according to the previous aspect, the apparatus comprises an ion balancing solution bag (11) or syringe connected to an end of the ion replacement infusion line (74) for infusing the ion balancing solution into the patient or into the blood circuit (17).

In a 17$^{th}$ aspect according to anyone of the previous three aspects, the apparatus includes an ion replacement pump/syringe (75) operating on the ion replacement infusion line (74) to determine an ion balancing solution infusion rate ($Q_{ca}$).

In a 17$^{th}$ bis aspect according to anyone of the previous aspects, the apparatus includes a container of systemic anticoagulant (e.g., heparin) and an infusion line connected to the container of systemic anticoagulant and to the blood circuit (17), particularly upstream the filtration unit (2) to inject the systemic anticoagulant into the extracorporeal blood.

In an 18$^{th}$ aspect according to anyone of the previous aspects, said one or more lines (8; 51; 58; 63; 74) for infusing a respective solution into blood comprises an anticoagulant line (51) for directly infusing into the blood circuit (17) an anticoagulant solution including citrate and optionally including citric acid.

In a 19$^{th}$ aspect according to the previous aspect, the apparatus comprises an anticoagulant solution bag (10) connected to an end of the anticoagulant line (51) for infusing a solution including citrate, and optionally citric acid, into the blood circuit (17).

In a 20$^{th}$ aspect according to anyone of the previous two aspects, the anticoagulant line (51) is connected to the blood circuit (17) upstream the blood pump (21), said blood pump (21) operating on the blood withdrawal line (6).

In a 21$^{st}$ aspect according to any one of the previous three aspects, the apparatus includes an anticoagulant pump (54) operating on the anticoagulant line (51) to determine an anticoagulant infusion rate ($Q_{cit}$).

In a 22$^{nd}$ aspect according to any one of the previous aspects, the control unit (12) determines the parameter ($J_{buffer\_load}$/BW) indicative of a steady state acid-base balance in the blood of the patient based on one or more of, and in particular the three of:
- an estimation of an amount per unit of time of bicarbonate generated from metabolism of the bicarbonate precursor infused to the patient, in particular of citrate ($J_{met\_cit}$) and/or lactate ($J_{met\_lact}$);
- a bicarbonate balance ($J_{HCO3\_bal}$) from the CRRT blood treatment to be delivered in terms of an amount per unit of time;
- a lactate balance ($J_{lact\_bal}$) from the CRRT blood treatment to be delivered in terms of an amount per unit of time;
- an acid infusion ($J_{H+}$) from citric acid contained in the fluid source in terms of an amount per unit of time.

In a 23$^{rd}$ aspect according to the previous aspect, the control unit (12) determines the parameter indicative of a steady state acid-base balance in the blood of the patient based on an algebraic sum of the estimation of bicarbonate form precursor metabolism ($J_{met\_cit}$; $J_{lact}$), the bicarbonate balance ($J_{HCO3\_bal}$), and the acid infusion ($J_{H+}$), in particular the acid infusion ($J_{H+}$) being a negative term providing a loss in patient buffer.

In a 24$^{th}$ aspect according to the previous aspect, the control unit (12) determines the parameter ($J_{buffer\_load}$/BW) indicative of a steady state acid-base balance in the blood of the patient as follows:

$$nNBL = \frac{J_{buffer\_load}}{BW} = \frac{J_{met\_cit} + J_{HCO3\_bal} - J_{H+}}{BW}$$

alternatively, when also lactate balance is considered, the control unit (12) determines the parameter ($J_{buffer\_load}$/BW) indicative of a steady state acid-base balance in the blood of the patient as follows:

$$nNBL = \frac{J_{buffer\_load}}{BW} = \frac{J_{met\_cit} + J_{HCO3\_bal} + J_{lact\_bal} - J_H +}{BW}$$

In a 25$^{th}$ aspect according to any one of the previous aspects, the control unit (12) determines the parameter ($J_{buffer\_load}$/BW) indicative of a steady state acid-base balance in the blood of the patient (or determines the parameter ($Cp_{HCO3\_pat}$) indicative of a steady state bicarbonate concentration in the blood of the patient) based on an acid infusion ($J_{H+}$) from citric acid contained in the fluid source in terms of an amount per unit of time, wherein the acid infusion ($J_{H+}$) is a function of a citric acid concentration ($C_{citric\_pbp}$) and of an infusion rate ($Q_{cit}$) of citric acid, in particular the acid infusion ($J_{H+}$) being equal to 3 times the citric acid concentration ($C_{citric\_pbp}$) multiplied by the infusion rate ($Q_{cit}$) of citric acid.

In a 26$^{th}$ aspect according to any one of the previous aspects, the control unit (12) determines the parameter ($J_{buffer\_load}$/BW) indicative of a steady state acid-base balance in the blood of the patient (or determines the parameter ($Cp_{HCO3\_pat}$) indicative of a steady state bicarbonate concentration in the blood of the patient) based on an estimation of an amount per unit of time of bicarbonate generated from metabolism of citrate ($J_{met\_cit}$) infused to the patient, in particular wherein the metabolism of citrate load leads to 3 moles of bicarbonate per mole of citrate at steady state, namely $J_{met\_cit} = 3 \cdot J_{cit\_load}$.

In a 27$^{th}$ aspect according to the previous aspect, the control unit (12) calculates the amount per unit of time of bicarbonate generated from metabolism of citrate, in particular the control unit calculates the citrate load ($J_{cit\_load}$) as a function of patient citrate metabolic clearance ($K_{cit\_met}$), in particular the metabolic clearance being based on, e.g., directly proportional to, a patient body weight (BW), for example being determined as follows:

$$K_{cit\_met} = 700 \cdot \frac{BW}{72}$$

wherein patient citrate metabolic clearance ($K_{cit\_met}$) is measured as [ml/min] and body weight (BW) is measured as [kg].

In a 28$^{th}$ aspect according to anyone of the previous two aspects, the amount per unit of time of bicarbonate generated from metabolism of citrate, in particular the control unit calculates the citrate load ($J_{cit\_load}$) is a function of citrate clearance ($K_{cit}$), in particular the control unit (12) determining the citrate clearance ($K_{cit}$) as a function of one or more flow rates, particularly including one or more of dialysis flow rate ($Q_d$), plasma water flow rate ($Qpw_{inlet}$), ultrafiltration rate ($Q_{fil}$) in filtration unit (2).

In a 29$^{th}$ aspect according to the previous aspect, the control unit (12) determines the citrate clearance ($K_{cit}$) as a function of the filtration unit (2) intended for CRRT treatment, in particular as a function of a sieving coefficient ($SC_{cit}$) for citrate and/or a ratio of filtration unit surface area to diffusive mass transfer resistance ($S/RT_{cit}$) for citrate.

In a 30$^{th}$ aspect according to anyone of the previous two aspects, the control unit (12) determines the citrate clearance ($K_{cit}$) according to the following relationships:

$$K_{cit} = \frac{Qpw_{inlet} \cdot Q_d - f_{cit} \cdot (Qpw_{inlet} - SC_{cit} \cdot Q_{fil}) \cdot (Q_d + SC_{cit} \cdot Q_{fil})}{Q_d - f_{cit} \cdot (Qpw_{inlet} - SC_{cit} \cdot Q_{fil})}$$

$$f_{cit} = \left(\frac{Qpw_{inlet} - SC_{cit} \cdot Q_{fil}}{Qpw_{inlet}} \cdot \frac{Q_d + SC_{cit} \cdot Q_{fil}}{Q_d}\right)^{\frac{1}{\gamma_{cit}}}$$

$$\gamma_{cit} = e^{\left(\frac{SC_{cit} \cdot Q_{fil}}{\frac{S}{RT_{cit}}}\right)} - 1$$

$$Qpw_{inlet} = Qpw + Q_{cit} + Q_{rep\_pre} = Q_b \cdot (1 - Hct) \cdot Fp + Q_{cit} + Q_{rep\_pre}$$

the notations being included in the glossary.

In a 31$^{st}$ aspect according to any one of the previous five aspects, the control unit (12) calculates the amount per unit of time of bicarbonate generated from metabolism of citrate ($J_{met\_cit}$) as a function of plasma water flow rate ($Qpw_{inlet}$) at filtration unit inlet and/or plasma flow rate (Qp), in particular the control unit (12) determining the plasma water flow rate ($Qpw_{inlet}$) at filtration unit inlet according to the following formula:

$$Qpw_{inlet} = Qpw + Q_{cit} + Q_{rep\_pre} = Q_b \cdot (1-Hct) \cdot Fp + Q_{cit} + Q_{rep\_pre}$$

the notations being included in the glossary.

In a 32$^{nd}$ aspect according to anyone of the previous six aspects, the control unit (12) calculates the amount per unit of time of bicarbonate generated from metabolism of citrate, in particular the control unit calculates the citrate load ($J_{cit\_load}$) alternatively as a function of citrate dose ($D_{cit}$) and blood flow (Qb), namely according to $D_{cit} \cdot Q_b$, or as a function of citrate flow rate ($Q_{cit}$) in an anticoagulant line (51) and total citrate concentration ($C_{cit\_pbp}$), namely according to $Q_{cit} \cdot C_{cit_{PBP}}$.

In a 33$^{rd}$ aspect according to anyone of the previous seven aspects, the control unit (12) calculates the amount per unit of time of bicarbonate generated from metabolism of citrate ($J_{met\_cit}$) according to the following formula:

$$3 \cdot D_{cit} \cdot Q_b \cdot \left(1 - \frac{K_{cit}}{Qpw_{inlet}}\right) \cdot \left(1 - \frac{1}{1 + \frac{K_{cit\_met}}{K_{cit}} \cdot \frac{Qpw_{inlet}}{Qp}}\right)$$

In a 33$^{rd}$ bis aspect according to anyone of the previous eight aspects, the control unit (12) calculates the amount per unit of time of bicarbonate generated from metabolism of citrate ($J_{met\_cit}$) according to the following formula:

$$3 \cdot D_{cit} \cdot Q_b \cdot \left(1 - \frac{K_{cit}}{Qpw_{inlet}}\right)$$

assuming patient systemic concentration $Cp_{cit\_pat}$ equal to zero.

In a 34$^{th}$ aspect according to any one of the previous aspects, the control unit (12) determines the parameter ($J_{buffer\_load}$/BW) indicative of a steady state acid-base balance in the blood of the patient based on a bicarbonate balance ($J_{HCO3\_bal}$) from the CRRT blood treatment to be delivered in terms of an amount per unit of time, in particular wherein the bicarbonate balance ($J_{HCO3\_bal}$) is the difference between an infusion rate from the dialysis fluid and/or the replacement fluid ($J_{HCO3\_inf}$) and the bicarbonate removal into dialysate ($J_{HCO3\_dial}$).

In a 35th aspect according to the previous aspect, the control unit (12) calculates the bicarbonate balance ($J_{HCO3\_bal}$) as a function of replacement flow rate ($Q_{rep}$) and bicarbonate concentration in the replacement solution ($C_{HCO3\_rep}$), namely as a function of $Q_{rep} \cdot C_{HCO3\_rep}$.

In a 36th aspect according to any one of the previous two aspects, the control unit (12) calculates the bicarbonate balance ($J_{HCO3\_bal}$) as a function of bicarbonate clearance ($K_{KHCO3}$), in particular the control unit (12) determining the bicarbonate clearance ($K_{KHCO3}$) as a function of one or more flow rates, particularly including one or more of dialysis flow rate ($Q_d$), blood water flow rate ($Qbw_{inlet}$), ultrafiltration rate ($Q_{fil}$) in filtration unit (2).

In a 37th aspect according to the previous aspect, the control unit (12) calculates the bicarbonate clearance ($K_{HCO3}$) as a function of the filtration unit (2) intended for CRRT treatment, in particular as a function of a sieving coefficient ($SC_{HCO3}$) for bicarbonate and/or a ratio of filtration unit surface area to diffusive mass transfer resistance ($S/RT_{HCO3}$) for bicarbonate.

In a 38th aspect according to anyone of the previous two aspects, the control unit (12) is configured to determine the bicarbonate clearance ($K_{HCO3}$) according to the following relationships:

$$K_{HCO3} = \frac{f_{HCO3} \cdot (Qbw_{inlet} - SC_{HCO3} \cdot Q_{fil}) \cdot (Q_d + SC_{HCO3} \cdot Q_{fil})}{Q_d - f_{HCO3} \cdot (Qbw_{inlet} - SC_{HCO3} \cdot Q_{fil})}$$

$$f_{HCO3} = \left(\frac{Qbw_{inlet} - SC_{HCO3} \cdot Q_{fil}}{Qbw_{inlet}} \cdot \frac{Q_d + SC_{HCO3} \cdot Q_{fil}}{Q_d}\right)^{\frac{1}{\gamma_{HCO3}}}$$

$$\gamma_{HCO3} = e^{\left(\frac{SC_{HCO3} \cdot Q_{fil}}{\frac{S}{RT_{HCO3}}}\right)} - 1$$

$$Qbw_{inlet} = Q_{bw} + Q_{cit} + Q_{rep\_pre} = Q_b \cdot [(1 - Hct) \cdot Fp + Hct \cdot Frbc] + Q_{cit} + Q_{rep\_pre}$$

the notations being included in the glossary.

In a 39th aspect according to anyone of the previous five aspects, the control unit (12) is configured to calculate the bicarbonate balance ($J_{HCO3\_bal}$) as a function of blood water flow rate ($Qbw_{inlet}$) at filtration unit inlet and/or blood water flow rate ($Q_{bw}$), in particular the control unit (12) determining the blood water flow rate ($Qbw_{inlet}$) at filter inlet according to the following formula:

$$Qbw_{inlet} = Q_{bw} + Q_{cit} + Q_{rep\_pre} = Q_b \cdot [(1-Hct) \cdot Fp + Hct \cdot Frbc] + Q_{cit} + Q_{rep\_pre}$$

the notations being included in the glossary.

In a 40th aspect according to anyone of the previous five aspects, the control unit (12) calculates the bicarbonate balance ($J_{HCO3\_bal}$) as a function of bicarbonate plasma water concentration at filter inlet ($Cpw_{HCO3\_inlet}$), in particular as a function of a difference between bicarbonate plasma water concentration at filter inlet ($Cpw_{HCO3\_inlet}$) and bicarbonate concentration in the dialysis fluid ($C_{HCO3\_d}$).

In a 41st aspect according to anyone of the previous six aspects, the control unit (12) calculates the bicarbonate balance ($J_{HCO3\_bal}$) as a function of bicarbonate concentration in the dialysis fluid ($C_{HCO3\_d}$), in particular as a function of a difference between bicarbonate plasma water concentration at filter inlet ($Cpw_{HCO3\_inlet}$) and bicarbonate concentration in the dialysis fluid ($C_{HCO3\_d}$).

In a 42nd aspect according to anyone of the previous two aspects, the control unit (12) is configured to calculate the bicarbonate plasma water concentration at filter inlet ($Cpw_{HCO3\_inlet}$) as a function of flow rates including one or more of blood water flow rate ($Q_{bw}$), blood water flow rate at filter inlet ($Qbw_{inlet}$) and pre replacement infusion flow rate ($Q_{rep\_pre}$) and/or as a function of bicarbonate concentrations including one or more of bicarbonate concentration in the replacement solution ($C_{HCO3\_rep}$) and patient plasma bicarbonate concentration ($Cp_{HCO3_{pat}}$).

In a 43rd aspect according to any one of the previous eight aspects, the control unit (12) calculates the bicarbonate balance ($J_{HCO3\_bal}$) as a function of ultrafiltration rate ($Q_{fil}$) in filtration unit (2) and bicarbonate concentration in the dialysis fluid ($C_{HCO3\_d}$), namely as a function of $Q_{fil} \cdot C_{HCO3\_d}$.

In a 44th aspect according to anyone of the previous nine aspects, the control unit (12) is configured to calculate the bicarbonate balance ($J_{HCO3\_bal}$) according to the following formula:

$$J_{HCO3\_bal} = Q_{rep} \cdot C_{HCO3\_rep} + \frac{Qbw_{inlet} \cdot Q_d - f_{HCO3} \cdot (Qbw_{inlet} - SC_{HCO3} \cdot Q_{fil}) \cdot (Q_d + SC_{HCO3} \cdot Q_{fil})}{Q_d - f_{HCO3} \cdot (Qbw_{inlet} - SC_{HCO3} \cdot Q_{fil})} \cdot$$
$$\left(Cpw_{HCO3\_inlet} - C_{HCO3\_d}\right) + Q_{fil} \cdot C_{HCO3\_d}$$

In a 45th aspect according to anyone of the previous aspects, the control unit (12) determines the parameter ($J_{buffer\_load}/BW$) indicative of a steady state acid-base balance in the blood of the patient (or determines the parameter ($Cp_{HCO3\_pat}$) indicative of a steady state bicarbonate concentration in the blood of the patient) based on a lactate balance ($J_{lact\_bal}$) from the CRRT blood treatment to be delivered in terms of an amount per unit of time, in particular wherein the lactate balance ($J_{lact\_bal}$) is the difference between a lactate infusion rate from the dialysis fluid and/or the replacement fluid ($J_{lact\_inf}$) and the lactate removal into dialysate ($J_{lact\_dial}$).

In a 46th aspect according to the previous aspect, the control unit (12) calculates the lactate balance ($J_{lact\_bal}$) as a function of replacement flow rate ($Q_{rep}$) and lactate concentration in the replacement solution ($C_{lact\_rep}$), namely as a function of $Q_{rep} \cdot C_{lact\_rep}$.

In a 47th aspect according to anyone of the previous two aspects, the control unit (12) calculates the lactate balance ($J_{lact\_bal}$) as a function of lactate clearance ($K_{lact}$), in particular the control unit (12) determining the lactate clearance ($K_{lact}$) as a function of one or more flow rates, particularly including one or more of dialysis flow rate ($Q_d$), blood water flow rate ($Qbw_{inlet}$), ultrafiltration rate (Qfil) in filtration unit (2).

In a 48th aspect according to previous aspect, the control unit (12) calculates the lactate clearance ($K_{lact}$) as a function of the filtration unit (2) intended for CRRT treatment, in particular as a function of a sieving coefficient ($SC_{lact}$) for lactate and/or a ratio of filtration unit surface area to diffusive mass transfer resistance ($S/RT_{lact}$) for lactate.

In a 49th aspect according to anyone of the previous two aspects, the control unit (12) is configured to determine the lactate clearance ($K_{lact}$) according to the following relationships:

$$K_{lact} = \frac{Qbw_{inlet} \cdot Q_d - f_{lact} \cdot (Qbw_{inlet} - SC_{lact} \cdot Q_{fil}) \cdot (Q_d + SC_{lact} \cdot Q_{fil})}{Q_d - f_{lact} \cdot (Qbw_{inlet} - SC_{lact} \cdot Q_{fil})}$$

-continued $$f_{lact} = \left(\frac{Qbw_{inlet} - SC_{lact} \cdot Q_{fil}}{Qbw_{inlet}} \cdot \frac{Q_d + SC_{lact} \cdot Q_{fil}}{Q_d}\right)^{\frac{1}{\gamma_{lact}}}$$

$$\gamma_{lact} = e^{\left(\frac{SC_{lact} \cdot Q_{fil}}{\frac{S}{RT_{lact}}}\right)} - 1$$

$$Qbw_{inlet} =$$

$$Q_{bw} + Q_{cit} + Q_{rep\_pre} = Q_b \cdot [(1 - Hct) \cdot Fp + Hct \cdot Frbc] + Q_{cit} + Q_{rep\_pre}$$

the notations being included in the glossary.

In a 50$^{th}$ aspect according to anyone of the previous five aspects, the control unit (12) calculates the lactate balance ($J_{lact\_bal}$) as a function of blood water flow rate ($Qbw_{inlet}$) at filtration unit inlet and/or blood water flow rate (Qbw), in particular the control unit (12) determining the blood water flow rate ($Qbw_{inlet}$) at filter inlet according to the following formula:

$$Qbw_{inlet} = Q_{bw} + Q_{cit} + Q_{rep\_pre} = Q_b \cdot [(1-Hct) \cdot Fp + Hct \cdot Frbc] + Q_{cit} + Q_{rep\_pre}$$

the notations being included in the glossary.

In a 51$^{st}$ aspect according to any one of the previous six aspects, the control unit (12) calculates the lactate balance ($J_{lact\_bal}$) as a function of lactate plasma water concentration at filter inlet ($Cpw_{lact\_inlet}$), in particular as a function of a difference between lactate plasma water concentration at filter inlet ($Cpw_{lact\_inlet}$) and lactate concentration in the dialysis fluid ($C_{lact\_d}$).

In a 52$^{nd}$ aspect according to any one of the previous seven aspects, the control unit (12) calculates the lactate balance ($J_{lact\_bal}$) as a function of lactate concentration in the dialysis fluid ($C_{lact\_d}$), in particular as a function of a difference between lactate plasma water concentration at filter inlet ($Cpw_{lact\_inlet}$) and lactate concentration in the dialysis fluid ($C_{lact\_d}$).

In a 53$^{rd}$ aspect according to anyone of the previous two aspects, the control unit (12) is configured to calculate the lactate plasma water concentration at filter inlet ($Cpw_{lact\_inlet}$) as a function of flow rates including one or more of blood water flow rate ($Q_{bw}$), blood water flow rate at filter inlet ($Qbw_{inlet}$) and pre replacement infusion flow rate ($Q_{rep\_pre}$) and/or as a function of lactate concentrations including one or more of lactate concentration in the replacement solution ($C_{lact\_rep}$) and patient plasma lactate concentration ($Cp_{lact\_pat}$).

In a 54$^{th}$ aspect according to any one of the previous eight aspects, the control unit (12) calculates the lactate balance ($J_{lact\_bal}$) as a function of ultrafiltration rate (Qfil) in filtration unit (2) and lactate concentration in the dialysis fluid ($C_{lact\_d}$), namely as a function of $Q_{fil} \cdot C_{lact\_d}$.

In a 55$^{th}$ aspect according to any one of the previous nine aspects, the control unit (12) calculates the lactate balance ($J_{lact\_bal}$) according to the following formula:

$$J_{lact\_bal} = Q_{rep} \cdot C_{lact\_rep} + \frac{Qbw_{inlet} \cdot Q_d - f_{lact} \cdot (Qbw_{inlet} - SC_{lact} \cdot Q_{fil}) \cdot (Q_d + SC_{lact} \cdot Q_{fil})}{Q_d - f_{lact} \cdot (Qbw_{inlet} - SC_{lact} \cdot Q_{fil})} \cdot$$
$$(Cpw_{lact\_inlet} - C_{lact\_d}) + Q_{fil} \cdot C_{lact\_d}$$

In a 56$^{th}$ aspect according to anyone of the previous aspects, the control unit (12) is configured to compare the parameter indicative of a steady state acid-base balance in the blood of the patient (or to compare the parameter ($Cp_{HCO3\_pat}$) indicative of a steady state bicarbonate concentration in the blood of the patient) with a threshold, in case the threshold is an upper threshold, the control unit (12) generating an alert when the parameter is higher than the upper threshold, in case the threshold is a lower threshold, the control unit (12) generating an alert when the parameter is lower than the lower threshold.

In a 57$^{th}$ aspect according to the previous aspect, in case the parameter exceeds the threshold, the control unit (12) is configured to either issue the alert and keep an entered patient prescription, or to issue the alert and refuse the entered patient prescription, in particular wherein in case the entered prescription is refused, the control unit (12) is further configured to:
restore a previous valid patient prescription; or
automatically shift one or more parameters of the patient prescription, such as a blood flow rate, and/or a citrate dose, to a proposed value defining a new valid patient prescription.

In a 58$^{th}$ aspect according to anyone of the previous two aspects, assuming a target set for steady state patient bicarbonate concentration, in particular equal to 25 mmol, the threshold includes an upper threshold comprised between 0.25 and 0.5 mmol/h/kg, in particular.
a first upper threshold (nNBL1) is comprised between 0.25 and 0.35 mmol/h/kg, for example the first threshold (nNBL1) being about 0.3 mmol/h/kg; and/or
a second upper threshold (nNBL2) is comprised between 0.35 and 0.5 mmol/h/kg, more in detail between 0.4 and 0.45 mmol/h/kg, for example the second threshold (nNBL2) being about 0.4 mmol/h/kg.

In a 59$^{th}$ aspect according to anyone of the previous three aspects, the threshold includes a lower threshold comprised between 0 and −0.2 mmol/h/kg, in particular the lower threshold (nNBL2) being about −0.1 mmol/h/kg, the control unit (12) being further configured to issue and alert and/or to block an entered prescription in case the parameter is lower than the lower threshold.

In a 60$^{th}$ aspect according to anyone of the previous aspects, the control unit (12) is configured to compare the parameter indicative of a steady state acid-base balance in the blood of the patient with a first upper threshold (nNBL1) and/or with a second upper thresholds (nNBL2) higher than the first upper threshold (nNBL1), wherein, in case the parameter is higher than the first upper threshold (nNBL1) and lower than the second upper threshold (nNBL2), the control unit (12) is configured to issue an alert, in particular an entered patient prescription remaining acceptable, in case the parameter is higher than the second upper threshold (nNBL2), the control unit (12) is configured to refuse the entered patient prescription.

In a 61$^{st}$ aspect according to anyone of the previous aspects, the control unit (12) is configured to determine the parameter indicative of a steady state acid-base balance in the blood of the patient (or to determine the parameter ($Cp_{HCO3\_pat}$) indicative of a steady state bicarbonate concentration in the blood of the patient) before starting the CRRT blood treatment.

In a 62$^{nd}$ aspect according to anyone of the previous aspects, the control unit (12) is configured to receive the patient prescription parameters, and to determine the parameter indicative of a steady state acid-base balance in the blood of the patient (or to determine the parameter ($Cp_{HCO3\_pat}$) indicative of a steady state bicarbonate concentration in the blood of the patient) based on one or more of the prescription parameters or based on parameters directly derived from the prescription parameters.

In a 63$^{rd}$ aspect according to anyone of the previous aspects, the control unit (12) receives the patient prescription including one or more of a blood flow rate ($Q_b$) in the blood circuit (17), a dialysis flow rate ($Q_d$) of dialysis fluid in a dialysis supply line (8), a patient fluid removal rate ($Q_{wt}$) to be removed from the patient, and a dialysate flow rate ($Q_{dial}$), in particular the control unit (12) being configured to receive patient prescription parameters comprising the blood flow rate ($Q_b$) in the blood circuit (17), the dialysis flow rate ($Q_d$) of dialysis fluid in the dialysis supply line (8) and the patient fluid removal rate ($Q_{wt}$) to be removed from the patient.

In a 64$^{th}$ aspect according to anyone of the previous aspects, the control unit (12) is configured to receive patient prescription parameters comprising:
- a fluid flow rate of a replacement fluid ($Q_{rep}$), i.e. a total flow rate of replacement fluid infused pre and post filtration unit (2), and a pre or post infusion ratio (PRE %) of replacement fluid; or
- a post-infusion flow rate of a substitution fluid ($Q_{post}$) and/or a pre-infusion flow rate of a substitution fluid ($Q_{pre}$).

In a 65$^{th}$ aspect according to anyone of the previous aspects, the control unit (12) is configured to receive patient prescription parameters comprising a calcium compensation parameter (CaComp), i.e. a relative dosage of calcium infusion to compensate for an estimated calcium loss in dialysate fluid, expressed in percentage.

In a 66$^{th}$ aspect according to anyone of the previous aspects, the control unit (12) is configured to determine the parameter indicative of a steady state acid-base balance in the blood of the patient ignoring lactate impact.

In a 67$^{th}$ aspect according to anyone of the previous aspects, the control unit (12) is configured to determine the parameter indicative of a steady state acid-base balance in the blood of the patient imposing a constant value for patient plasma bicarbonate concentration ($Cp_{HCO3\_pat}$), said constant value being for example 25 mM.

In a 67$^{th}$ bis aspect according to anyone of the previous aspects, the control unit (12) is configured to determine the parameter ($Cp_{HCO3\_pat}$) indicative of a steady state bicarbonate concentration in the blood of the patient imposing a constant value for the normalized net buffer load (NBL) for the patient at steady state said constant value being for example 0.1 mmol/h/kg.

In a 68$^{th}$ aspect according to anyone of the previous aspects, the control unit (12) is configured to determine the parameter indicative of a steady state acid-base balance in the blood of the patient (or to determine the parameter ($Cp_{HCO3\_pat}$) indicative of a steady state bicarbonate concentration in the blood of the patient) imposing a constant value for patient plasma lactate concentration (Cplact), said constant value being for example 1.5 mM.

In a 69$^{th}$ aspect according to anyone of the previous aspects, the parameter indicative of a steady state acid-base balance in the blood of the patient is the net buffer load balance expected at a steady state where patient plasma bicarbonate ($Cp_{HCO3\_pat}$) is stabilized at a set constant value, e.g. 25 mM.

In a 70$^{th}$ aspect according to anyone of the previous aspects, the control unit (12) receives an estimated fixed value for the patient systemic steady state concentration of bicarbonate, in particular 25 mM.

In a 71$^{st}$ aspect according to anyone of the previous aspects, the control unit (12) receives an estimated fixed value for the patient systemic steady state concentration of bicarbonate precursor, in particular for lactate, optionally said estimated fixed value being 1.5 mM.

In a 72$^{nd}$ aspect according to anyone of the previous aspects, the apparatus comprises a dialysis supply line (8) connected to an inlet of the secondary chamber (4).

In a 73$^{rd}$ aspect according to anyone of the previous aspects, the apparatus comprises a gas exchanger (46) for $CO_2$ removal having a blood inlet (46a) and a blood outlet (46b) connected to the blood circuit (17), the gas exchanger (46) being connected to the blood circuit (17) in series to the filtration unit (2).

In a 74$^{th}$ aspect according to anyone of the previous aspects, the control unit (12) is configured to calculate a citrate infusion flow rate ($Q_{cit}$), particularly based on blood flow ($Q_b$).

In a 75$^{th}$ aspect according to anyone of the previous aspects, the source of regional anticoagulant (10) comprises citrate, in particular trisodium citrate and optionally citric acid.

In a 76$^{th}$ aspect according to aspect 73 and to anyone of the previous aspects and, the gas exchanger (46) has a blood chamber and a gas chamber separated by a membrane, the gas exchanger comprising a gas inlet (52) and a gas outlet (53) in fluid communication with the gas chamber, the blood inlet (46a) and the blood outlet (46b) being in fluid communication with the blood chamber.

In a 77$^{th}$ aspect according to the previous aspect, the gas exchanger (46) is located upstream the filtration unit (2) connected and in fluid communication with the blood withdrawal line (6) or wherein the gas exchanger (46) is located downstream the filtration unit (2) connected and in fluid communication with the blood return line (7).

In a 78$^{th}$ aspect according to anyone of the previous aspects, the apparatus comprises a source of dialysis fluid for providing fluid to the dialysis supply line, the dialysis fluid being substantially free from calcium ions.

In a 79$^{th}$ aspect according to anyone of the previous aspects, the apparatus comprises a source of dialysis fluid including a buffer agent for providing fluid to the dialysis supply line, a buffer agent concentration in the dialysis fluid being comprised between 0 and 50 mmol/l, in particular between 10 mmol/l and 40 mmol/l.

In an 80$^{th}$ aspect according to anyone of the previous aspects 1-78, the apparatus comprises a source of dialysis fluid for providing fluid to the dialysis supply line, the dialysis fluid being substantially free from a buffer agent.

In an 80$^{th}$ bis aspect according to anyone of the previous aspects, the apparatus comprises a replacement solution bag (64) containing a substitute solution with a buffer agent, a buffer agent concentration in the substitute solution being comprised between 0 and 1000 mmol/l, in particular between 100 mmol/l and 200 mmol/l optionally in combination with buffer free dialysate and/or buffer free other replacement fluids, particularly between 50 mmol/l and 100 mmol/l optionally in combination with low buffer content in dialysate (e.g., <25 mmol/l) and/or low buffer content in other replacement fluids (e.g., <25 mmol/l), said one or more lines (8; 51; 58; 63; 74) for infusing a respective solution into blood comprises an infusion line (63) connected to the replacement solution bag (64) for infusing into the blood the substitute solution.

In an 80$^{th}$ ter aspect according to anyone of the previous aspects, the apparatus comprises a replacement solution bag (64) containing a substitute solution, the substitute solution being substantially free from a buffer agent, said one or more lines (8; 51; 58; 63; 74) for infusing a respective solution into blood comprises an infusion line (63) connected to the replacement solution bag (64) for infusing into the blood the substitute solution.

In an 80$^{th}$ quater aspect according to anyone of the previous aspects, wherein the buffer agent includes (and optionally is) bicarbonate.

In an 81$^{st}$ aspect according to anyone of the previous aspects, the apparatus comprises a dialysis pump (25) active on the dialysis supply line (8) and a control unit (12) operatively connected to the dialysis pump (25), the control unit being configured to drive the dialysis pump (25) to generate an dialysis flow rate ($Q_d$).

In an 82$^{nd}$ aspect according to anyone of the previous aspects, the apparatus comprises a dialysate pump (26) active on the dialysate line (13) and a control unit (12) operatively connected to the dialysate pump (26), the control unit being configured to drive the dialysate pump (26) to generate a dialysate flow rate ($Q_{dial}$).

In an 83$^{rd}$ aspect according to anyone of the previous aspects, the control unit (12) is operatively connected to the anticoagulant pump (10) to deliver an anticoagulant dose to the blood, the anticoagulant including citrate and the anticoagulant dose being comprised between 1.5 mmol/l and 6 mmol/l, in particular being included in the range between 2 mmol/l and 4 mmol/l and in detail being about 3 mmol/l.

In an 84$^{th}$ aspect according to any one of the previous aspects, the control unit (12) determines the parameter ($Cp_{HCO3\_pat}$) indicative of a steady state bicarbonate concentration in the blood of the patient, and more in detail bicarbonate losses in the dialysate ($J_{HCO3\_dial}$), based on one or more of, and in particular four of:

an estimation of an amount per unit of time of bicarbonate generated from metabolism of the bicarbonate precursor infused to the patient, in particular of citrate ($J_{met\_cit}$) and/or lactate ($J_{met\_lact}$);

a bicarbonate infusion ($J_{HCO3\_inf}$) from the CRRT blood treatment to be delivered in terms of an amount per unit of time;

a lactate balance ($J_{lact\_bal}$) from the CRRT blood treatment to be delivered in terms of an amount per unit of time;

a predefined net buffer load ($J_{buffer\_load}$), for example chosen between 0 and 0.35 mmol/h/kg, in particular 0.1 mmol/h/kg.

an acid infusion ($J_{H+}$) from citric acid contained in the fluid source in terms of an amount per unit of time.

In an 85$^{th}$ aspect according to the previous aspect, the control unit (12) determines the parameter ($Cp_{HCO3\_pat}$) indicative of a steady state bicarbonate concentration in the blood of the patient, and more in detail bicarbonate losses in the dialysate ($J_{HCO3\_dial}$), based on an algebraic sum of the estimation of bicarbonate form precursor metabolism ($J_{met\_cit}$; $J_{lact}$), the bicarbonate infusion ($J_{HCO3\_bal}$), the predefined net buffer load ($J_{buffer\_load}$), and the acid infusion ($J_{H+}$), in particular the acid infusion ($J_{H+}$) being a negative term providing a loss in patient buffer.

In an 86$^{th}$ aspect according to any one of the previous aspects, the control unit (12) determines the parameter ($Cp_{HCO3\_pat}$) indicative of a steady state bicarbonate concentration in the blood of the patient as a function of plasma water volume fraction (Fp) and/or blood water flow rate ($Q_{bw}$), particularly as a function of their ratio.

In an 87$^{th}$ aspect according to any one of the previous aspects, the control unit (12) determines the parameter ($Cp_{HCO3\_pat}$) indicative of a steady state bicarbonate concentration in the blood of the patient as a function of replacement fluid/flow rate/s ($Q_{rep\_pre}$) and/or bicarbonate concentration ($Cp_{HCO3rep}$) in the replacement fluid/s, in particular their product.

In an 88$^{th}$ aspect according to any one of the previous aspects, the control unit (12) determines the parameter ($Cp_{HCO3\_pat}$) indicative of a steady state bicarbonate concentration in the blood of the patient as a function of plasma water bicarbonate concentration at filter inlet ($Cpw_{HCO3_{inlet}}$) and/or blood water flow rate at the inlet ($Qbw_{inlet}$), in particular their product.

In an 89$^{th}$ aspect according to the previous aspect, the control unit (12) determines plasma water bicarbonate concentration at filter inlet ($Cpw_{HCO3_{inlet}}$) as a function of dialysis fluid flow rate ($Q_d$) and/or bicarbonate concentration ($C_{HCO3_{dial}}$) in the dialysis fluid, in particular their product.

In a 90$^{th}$ aspect according to any one of the previous aspects, the control unit (12) determines the parameter ($Cp_{HCO3\_pat}$) indicative of a steady state bicarbonate concentration in the blood of the patient as a function of an ultrafiltration rate ($Q_{fil}$) in the filtration unit (2) and/or bicarbonate concentration ($Cp_{HCO3_{dial}}$) in the dialysis fluid, in particular their product.

In a 91$^{st}$ aspect according to any one of the previous aspects, the control unit (12) determines the parameter ($Cp_{HCO3\_pat}$) indicative of a steady state bicarbonate concentration in the blood of the patient as a function of bicarbonate losses to dialysate ($J_{HCO3\_eff}$).

In a 92$^{nd}$ aspect according to any one of the previous aspects, the control unit (12) determines the parameter ($Cp_{HCO3\_pat}$) indicative of a steady state bicarbonate concentration in the blood of the patient as a function of bicarbonate clearance ($K_{HCO3}$).

In a 93$^{rd}$ aspect according to any one of the previous aspects, the control unit (12) determines the parameter ($Cp_{HCO3\_pat}$) indicative of a steady state bicarbonate concentration in the blood of the patient is the sum of bicarbonate concentration ($Cp_{HCO3_{dial}}$) in the dialysis fluid and an additional term function of one or more of dialysis fluid flow rate ($Q_d$) and/or bicarbonate concentration ($Cp_{HCO3_{dial}}$) in the dialysis fluid and/or an ultrafiltration rate ($Q_{fil}$) in the filtration unit (2) and/or bicarbonate losses to dialysate ($J_{HCO3\_eff}$) and/or bicarbonate clearance ($K_{HCO3}$).

Further characteristics and advantages of the present invention will better emerge from the detailed description that follows of some embodiments of the invention, illustrated by way of non-limiting example in the accompanying figures of the drawings.

BRIEF DESCRIPTION OF THE DRAWINGS

The description will now follow, with reference to the appended figures, provided by way of non-limiting example, in which.

DETAILED DESCRIPTION

As mentioned, extracorporeal blood treatment (dialysis) may be used in patients with rapidly developing loss of kidney function, called acute renal failure or slowly worsening kidney function, called Stage 5 chronic kidney disease (or end-stage renal disease). In the following description, some embodiments of extracorporeal blood treatment apparatuses will be firstly described being suitable, or designed, principally (though not exclusively) for intensive care treatments. The risk control measures, taken primarily to reduce the risk of developing metabolic alkalosis/acidosis in the patient, are thereafter described and may be implemented in any of the described embodiments as it is apparent from the following description.

Definitions

Unless defined otherwise, all technical and scientific terms used have the same meaning as commonly understood by one of ordinary skill in the art.

Figure 1:
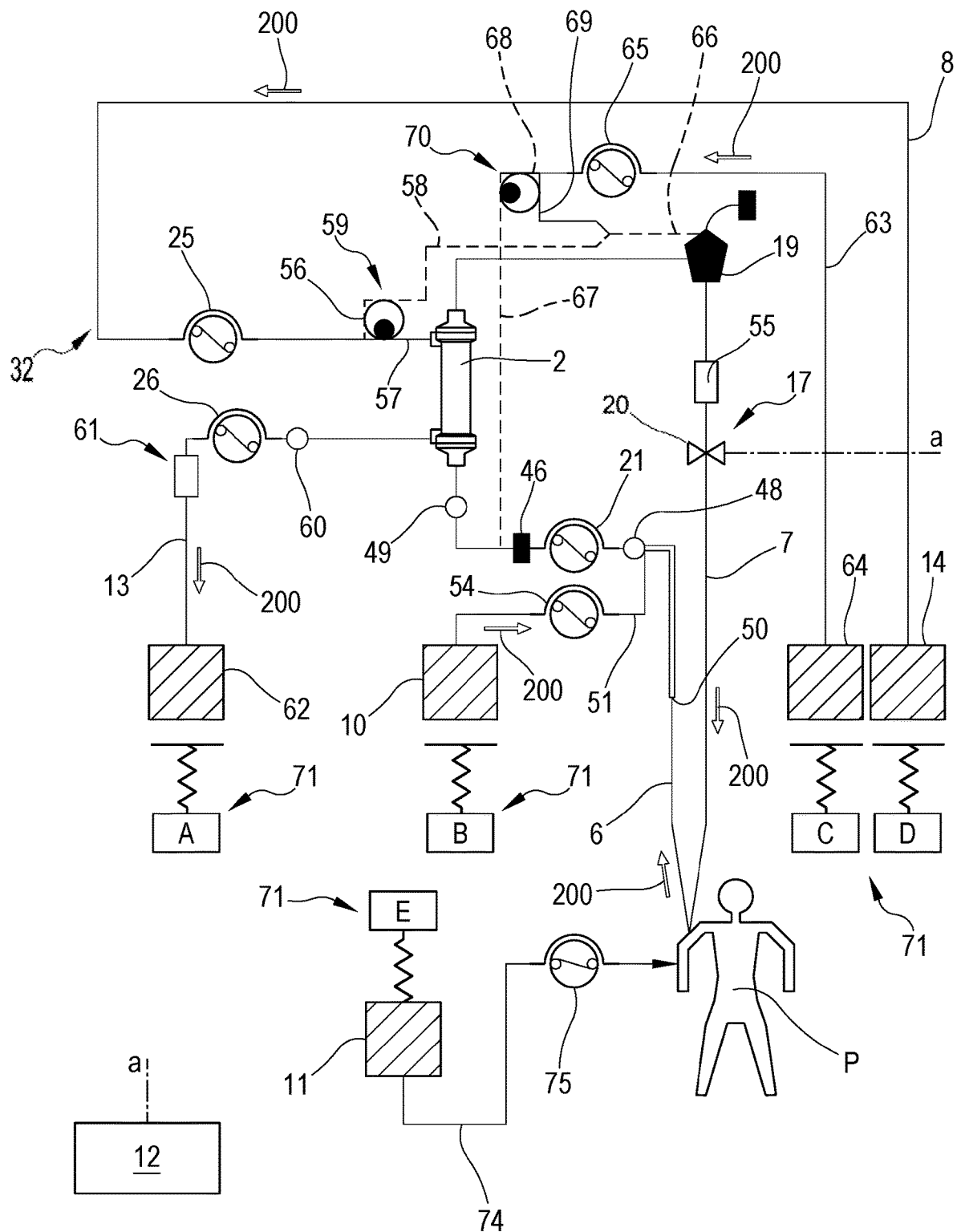
FIG. 1 schematically represents an extracorporeal blood treatment apparatus, particularly—but not exclusively— suitable for intensive care treatments (e.g., CRRT)

The term "downstream" refers to a position of a first component in a flow path relative to a second component wherein fluid will pass by the second component prior to the first component during normal operation. The first component can be said to be "downstream" of the second component, while the second component is "upstream" of the first component. FIG. 1 shows the fluid circulation directions (indicated with reference 200) during normal operation of the apparatus 1.

We define the "dialysis fluid" as the treatment fluid introduced to the second chamber of the filtration unit 2. The dialysis fluid may be on-line prepared or pre-packaged in sterile bags.

We define the "dialysate" as the fluid from the outlet from the second chamber of the filtration unit 2. Dialysate is the spent dialysis fluid, comprising the uremic toxins removed from the blood and may include ultrafiltrate fluid.

We define "regional anticoagulant" as a substance which, once mixed with extracorporeal blood, substantially prevents blood coagulation in the extracorporeal blood circuit and which is quickly metabolized by the patient, thus avoiding systemic anticoagulation.

We define "net buffer load" during the extracorporeal blood treatment (e.g., CRRT) the combination of bicarbonate generated from the metabolism of bicarbonate precursors, such as citrate and/or lactate infused into the patient ($J_{met\_cit}$; $J_{met\_lact}$), bicarbonate balance from the extracorporeal blood therapy ($J_{HCO3\_bal}$) which may match with net loss or net gain for the patient, and acid infusion, e.g., from citric acid content of the anticoagulant solution, when relevant. From the mathematical point of view, the general definition of net buffer load (mmol/h) used hereinafter is:

$$J_{buffer\_load} = J_{met\_cit} + J_{HCO3\_bal} + J_{met\_lact} - J_{H+}$$

We define "citrate dose" as the injected amount of citrate per liter of blood treated (mmol/L blood). We define patient "citrate load" as the rate at which citrate is returned to the patient (mmol/h).

$$J_{citrate\_load} = J_{cit\_PBP} - J_{cit\_eff}$$

We define "bicarbonate balance" as the net infusion or loss rate of bicarbonate in the extracorporeal blood treatment matching with the difference between the infusion rate from the dialysate and/or replacement fluids and the bicarbonate removal rate into dialysate.

$$J_{HCO3\_bal} = J_{HCO3\_inf} - J_{HCO3\_eff}$$

We define "calcium compensation" (or calcium compensation parameter) as the relative dosage of calcium infusion to compensate for the estimated calcium loss in dialysate, expressed in percentage.

We define "$K_0A$" as the mass transfer-area coefficient of a filtration unit, wherein $K_0$ is the clearance at infinite blood and dialysis fluid flow rates and A is the filtration unit surface area. "$K_0A$" is specific of a given solute and thereby changes according to the solute which is specifically considered.

In this application the term "citrate" means that the component is in form of a salt of citric acid, such as sodium, magnesium, calcium, or potassium salt thereof. The citric acid (denoted $C_6H_8O_7$) is deprotonated stepwise, therefore the "citrate" include all the different forms, citrate (denoted $C_6H_5O_7^{3-}$), hydrogen citrate (denoted $C_6H_6O_7^{2-}$), and dihydrogen citrate (denoted $C_6H_7O_7^{-}$).

The term "citrate" or "total citrate" means the total amount of citric acid and any salts thereof, such as its sodium, magnesium, calcium, or potassium salt thereof. In other terms, "total citrate" is the sum of free citrate ions and citrate containing complexes and ion pairs.

The term "buffer agent" means bicarbonate or bicarbonate precursors such as lactate, citrate or acetate.

Glossary

The following terms/parameters are consistently used throughout the equations provided in the following description of the detailed working of the extracorporeal blood treatment apparatus.

| Parameters | |
|---|---|
| BW | patient body weight (kg) |
| C | solute concentration (mM) |
| $C_{cit\_pbp}$ | total citrate concentration in citrate anticoagulation solution (sodium citrate + citric acid)-(mM) |
| $C_{citric\_pbp}$ | citric acid concentration in citrate anticoagulation solution-(mM) |
| Cp | plasma concentration (mM) |
| Cpw | plasma water concentration (mM) |
| $D_{cit}$ | citrate dose (mmol/L of blood) |
| Hct | haematocrit (dimensionless, $\in [0; 1]$) |
| J | mass transfer rate of solute (amount per unit of time) |
| K | clearance (ml/min) |
| $K_{cit\_met}$ | patient citrate metabolic clearance (ml/min) |
| nNBL | normalized Net Buffer Load (mmol/h/kg) |
| PRE | pre-infusion ratio of replacement flow (dimensionless, $\in [0; 1]$) |
| Q | flow rate (ml/min) |
| $Q_b$ | blood flow rate (ml/min) |
| $Q_{bw}$ | blood water flow rate (ml/min) |
| $Q_p$ | plasma flow rate (ml/min) |
| $Q_{pw}$ | plasma water flow rate (ml/min) |
| $Q_{fil}$ | ultrafiltration rate in CRRT filter (ml/min) |

-continued

| | |
|---|---|
| $Q_{wl}$ | patient fluid removal rate (ml/min) |
| $Q_d$ | Dialysis flow rate |
| $Q_{dial}$ | Dialysate flow rate |
| $Q_{ca}$ | Calcium/syringe flow rate (ml/min) |
| SC | sieving coefficient |
| S/RT | ratio of filter surface area to diffusive mass transfer resistance (ml/min) (↔'K0.A') |
| CaComp | calcium compensation parameter (dimensionless, ∈ [5%; 200%]) |
| Indices | |
| cit | citrate |
| $H_{CO3}$ | bicarbonate |
| lact | lactate |
| Ca | calcium |
| inlet | filter blood inlet |
| PBP | Pre Blood-Pump |
| d | Dialysis fluid |
| rep | replacement |
| rep_pre | pre-replacement infusion |
| dial | Dialysate |
| Constants | |
| $C_{HCO3fluid}$ = 22 mM | bicarbonate concentration in dialysis fluid and/or replacement fluids (when relevant)-(mM) |
| $Cp_{HCO3}$ = 25 mM | patient plasma bicarbonate concentration (mM) |
| $Cp_{lact}$ = 1.5 mM | patient plasma lactate concentration (mM) |
| nNBL0 = 0,1 mmol/h/kg | Set normalized net buffer load at patient steady state |
| $F_p$ = 0.95 | plasma water volume fraction |
| $F_{rbc}$ = 0.85 | intra erythrocyte water volume fraction |

Equations for Flow Rates

The following equations for flow rates express the relations between the flow rates which are used in the following detailed description.

The plasma water flow rate is function of blood flow rate as follows:

$$Qpw = Q_b \cdot (1-Hct) \cdot F_p$$

The blood water flow rate is function of blood flow rate as follows:

$$Qbw = Q_b \cdot (1-Hct) \cdot F_p + Hct \cdot Frbc$$

The ultrafiltration rate in the filtration unit is:

$$Q_{fil} = Q_{cit} + Q_{rep} + Q_{pf} + Q_{ca}$$

The pre-infusion rate of replacement fluid is:

$$Q_{rep\_pre} = PRE \cdot Q_{rep}$$

The dialysate flow rate is:

$$Q_{dial} = Q_{cit} + Q_d + Q_{rep} + Q_{pf} + Q_{ca}$$

Extracorporeal Blood Treatment Apparatus Particularly for CRRT Treatments

With reference to FIG. 1, the numeral 1 globally refers to the extracorporeal blood treatment apparatus, in particular for intensive care therapies. The apparatus according to FIG. 1 is particularly designed for continuous renal replacement therapies (CRRT). CRRT systems are configured for delivering very specific treatments designed for patients versing in acute states of illness and who have temporarily lost their kidney function in its entirety. In this respect, CRRT systems may be structurally and/or operationally different from extracorporeal blood treatment systems designed for chronic patient care. In contrast to chronic patients, acute patients temporarily experience complete loss of their kidney function typically due to a contemporaneous state of severe injury or during recovery from surgery. Consequently, acute patients are often extremely weak and typically not in a condition to be submitted to regular dialysis treatment, which could further deteriorate their state and lead to serious and possibly life-threatening complications. Under circumstances as described, CRRT systems are designed to individually treat a patient exhibiting very poor health, without inducing further stress to the patient body, in particular without allowing vital parameters pertaining to the patient's blood to deviate from ideal or near-ideal values. Within the scope of this document CRRT systems are, thus, inherently characterized by one or more of the following features. CRRT involves renal replacement therapy, meaning an adjuvant therapy aimed firstly at facilitating continuous fluid removal in diuretic-resistant or acute renal failure patients. Therefore, CRRT systems inherently require a continuous net fluid removal from the patient. In other words, a CRRT system requires a fluid balance control system, such as a weight loss control system, configured to generate a continuous net weight loss rate (as opposed to merely controlling parameters to enable achieving a desired target weight loss as typically found in chronic patient care). Furthermore, acute patients experience extravascular fluid overload, which cannot be safely removed within a short period of time (e.g. within a few hours of chronic treatment) without causing potentially severe consequences (e.g. hypovolemic shock, arrhythmia, hypoxemia, hypoventilation, etc.). Therefore, a CRRT system must inherently include a much more accurate control over system parameters, in particular flow rates, in order to ensure that the required low flow rates of both blood circulating extra-corporeally and of treatment fluid (infused in the extracorporeal circuit or diffused through the dialyzer) are used. Moreover, CRRT treatment is performed continuously (e.g. for days or even weeks, without interruption/with minimal interruptions). Therefore, treatment settings in CRRT are based on flow rate settings, rather than settings pertaining to some specified treatment time (which would be unknown as acute patients may require treatment for an unknown time). Consequently, operation of CRRT systems cannot be based on some pre-defined absolute weight loss to be achieved, but rather on a meticulously controlled fluid balance in the patient, requiring continuous adjustments to a number of operating parameters, which have to be controlled and maintained during the entire (and a priori unknown) treatment time, based on a set weight-loss rate. Additionally, CRRT renal replacement therapy involves therapy substituting kidney functions for a relatively long time period and, thus, a CRRT system further requires at least either fresh dialysis liquid exchange in the dialyzer (in order to remove unwanted substances from blood and to add desired substances to the blood by diffusion) and/or fresh infusion fluid in combination with ultrafiltration (in order to remove unwanted substances from blood and to add desired substances to the blood by convection).

At least for the reasons set forth above, CRRT systems need to exhibit specific technical features enabling the system to:

Allow setting of a weight loss rate,

Continuously remove excess water in accordance with a set weight loss rate,

Operate continuously at comparably low flow rates compatible with CRRT, and

Balance ion equilibrium by means of proper dialysis being performed and/or by means of substitution fluid continuously being delivered at controlled flow rates.

The apparatus 1 of FIG. 1 has an extracorporeal blood circuit 17, which takes blood from a patient P, for instance by means of a catheter introduced into a vein or artery of said patient, and through the blood withdrawal line 6 takes said blood, for instance continuously, to the filtration unit 2. The blood passes through the primary chamber of the filtration unit 2 and, through the blood return line 7, the treated blood is carried back to the patient. In the example of FIG. 1, the connection with an anticoagulant line 51 is provided immediately downstream from the blood collecting zone on the blood withdrawal line 6. In particular, the machine is equipped with source of regional anticoagulant 10, such as at least a secondary fluid container or bag for supplying the anticoagulant line 51; by using corresponding means for conveying fluid, in the example shown comprising an anticoagulant pump 54, for instance a peristaltic pump, it is possible to control the fluid flow within said line by introducing the regional anticoagulant directly into the blood by means of a direct connection to the blood withdrawal line 6. After defining a direction of fluid (blood) circulation 200 (during normal use of the apparatus) from the blood withdrawal line 6 towards the filtration unit 2 and from the latter through the blood return line 7 towards the patient P, a known blood pressure sensor 48, which shall not be described in further detail, is placed immediately downstream the anticoagulant line 51. The blood circuit 17 comprises means for conveying fluid, i.e. in this particular case at least a blood pump 21 for controlling and managing the suitable blood flow $Q_b$ in the circuit. Also the blood pump 21 is generally a peristaltic pump. Following the direction of blood circulation, a gas exchanger 46 for removing $CO_2$ from circulating blood may be connected to the blood circuit. The gas exchanger 46 is in fluid communication with the blood circuit 17 to receive extracorporeal blood, allow $CO_2$ removal from blood and returning blood to the blood circuit at a downstream point. FIG. 1 shows a gas exchanger 46 placed upstream the filtration unit 2; however, the gas exchanger may be alternatively positioned downstream the filtration unit along blood circulation direction. Blood circulation direction during normal use of the apparatus is indicated in FIG. 1 with an arrow which also represent the blood flow rate $Q_b$ direction. The gas exchanger 46 is connected in series with the filtration unit 2 and is placed downstream the injection point 50 where the regional anticoagulation solution is delivered to extracorporeal blood. The gas exchanger 46 has a blood chamber and a gas chamber separated by a membrane permeable to gases, in particular $CO_2$; the gas exchanger comprise a gas inlet, which can be connected to a gas source, such as the medical gas supply system in a hospital to receive pressurized air or oxygen for example, and a gas outlet in fluid communication with the gas chamber to discharge exhausted gas having removed $CO_2$ from extracorporeal blood. The blood inlet and the blood outlet put the extracorporeal blood circuit 17 in fluid communication with the gas exchanger blood chamber.

Then, the blood passes through another pressure sensor 49 controlling the correct flow within the blood circuit. After passing through the primary chamber of the filtration unit 2, where the suitable exchanges of substances, molecules and fluids occur by means of a semipermeable membrane, the treated blood enters the blood return line 7, first passing through the air separator 19, commonly known as "bubble trap", designed so as to ensure the detection and removal of air bubbles present in the blood. The treated blood getting out of the air separator 19 then passes through an air bubble sensor 55 verifying the absence of said dangerous formations within the treated blood that has to be re-introduced in the patients blood circulation. Immediately downstream from the bubble sensor 55, the safety valve 20 (or venous clamp) is placed which, in case of alarm, can block the blood flow towards the patient. In particular, should the bubble sensor 55 detect the presence of anomalies in the blood flow, the machine through safety valve 20 would be able to block immediately the passage of blood so as to avoid any consequence to the patient. Downstream from the safety valve 20, the treated blood is then carried back to the patient P undergoing therapy. The extracorporeal blood treatment apparatus of FIG. 1 is equipped with a dialysis fluid circuit 32, which is also provided with at least a dialysis supply line 8 leading into the filtration unit 2 and with a dialysate line 13 from the filtration unit. At least a primary fluid container, defining said dialysis liquid source 14, is designed to supply the supply line 8 of the dialysis fluid circuit 32 (generally the primary fluid container shall consist of one or more bags containing a suitable dialysis liquid). The supply line 8 includes means for conveying fluid such as at least a dialysis fluid pump 25 (in the embodiment of FIG. 1 a peristaltic pump) for controlling the flow rate $Q_d$ of dialysis liquid from the bag and for defining a direction 200 of dialysis fluid circulation. Downstream from the dialysis fluid pump 25 in the direction of circulation 200 there is a branching 56 splitting the dialysis supply line 8 up into an intake branch 57 and an infusion branch 58. In particular, the infusion branch 58 is connected to the blood return line 7 of the blood circuit 17. In other words, by means of said infusion branch 58 it is possible to obtain a post-infusion directly in the blood line 17 using the content of the primary fluid container. Conversely, the intake branch 57 conveys the fluid directly to the filtration unit 2 and in particular to the secondary chamber of said unit. The dialysis fluid circuit 32 is further equipped with selecting means 59 for determining the percentages of fluid flow within the infusion branch 58 and the intake branch 57. Generally said selecting means 59, usually placed near the branching 56, can be positioned at least between a first operating condition in which they allow the passage of fluid in the intake branch 57 and block the passage in the infusion branch 58, and a second operating condition in which they allow the passage of fluid in the infusion branch 58 and block the passage in the intake branch 57. In other words, said selecting means 59 may consist of a valve element operating on the dialysis fluid circuit 32 by alternatively blocking the passage of fluid in either branch. Suitable selectors may be alternatively provided, which are able to establish a priori the amount of liquid that has to pass through both branches simultaneously. It will also be possible to vary the percentages of fluid in either branch as a function of time and of the pre-established therapies. The dialysis liquid through the intake branch 57 gets into the secondary chamber of the filtration unit 2. In particular, the primary chamber through which the blood flow passes is separated from the secondary chamber through which the dialysis liquid passes by means of the semipermeable membrane ensuring the suitable passage of the dangerous substances/molecules and of fluid from the blood towards the dialysis liquid mainly by means of convection and diffusion processes, and also ensuring through the same principles the passage of substances/molecules from the dialysis liquid towards the blood. The dialysis fluid then gets into the dialysate line 13 and passes through a suitable dialysate pressure sensor 60. Means is provided for conveying fluid, for instance a dialysate pump 26 controlling the flow rate $Q_{dial}$ in the dialysate line 13 within the fluid circuit 32. Also said pump will generally be a peristaltic pump. The fluid to be eliminated then passes through a blood detector 61 and is conveyed into a collection container or bag 62. The hydraulic circuit of the apparatus according to FIG. 1 includes at least another infusion line 63 for feeding fluid into the blood return line 7 of the blood circuit 17. In particular, the infusion fluid is taken from at least an auxiliary container 64 and is sent directly to the blood return line 7 of the blood circuit 17 through means for conveying fluid, generally an infusion pump 65 (in the example a peristaltic pump) controlling its flow rate $Q_{rep}$—total replacement flow rate. In particular, the infusion liquid can be introduced directly into the air separator 19. As can also be inferred, the infusion branch 58 of the dialysis fluid circuit 32 and the infusion line 63 are equipped with a common end length 66 letting fluid to enter into the blood circuit 17. Said intake end length 66 is placed downstream from the infusion pump 65 with respect to a direction of infusion and carries the fluid directly into the air separator 19. Further, referring to the diagram in FIG. 1, the infusion line 63 comprises at least a pre-infusion branch 67 connected to the blood withdrawal line 6 of the blood circuit 17. In further detail, downstream from the infusion pump 65 with respect to the direction of infusion, there is an infusion branching 68 splitting the infusion line 63 up into the pre-infusion branch 67 and post-infusion branch 69. The pre-infusion branch 67, in particular, carries the fluid taken from the bag 64 into the blood withdrawal line 6 of the blood circuit 17 downstream from the blood pump 21 and downstream the gas exchanger 46 with respect to the direction of blood circulation. Conversely, the post-infusion branch 69 is connected directly to the common end length 66. The infusion line 63 further comprises selecting means 70 for determining the percentage of liquid flow to be sent to the post-infusion branch 69 and to the pre-infusion branch 67. The selecting means 70 placed near the branching 68 may be switched between at least a first operating condition in which they allow the passage of fluid in the pre-infusion branch 67 and block the passage in the post-infusion branch 69, and at least a second operating condition in which they allow the passage of fluid in the post-infusion branch 69 and block the passage in the pre-infusion branch 67. Obviously, as in the case of the selecting means 59 present on the dialysis fluid circuit 32, also the other selecting means 70 will be able to determine the percentage of fluid that has to pass in each of the two branches and to possibly vary it in time in accordance with the planned therapies. Moreover, the selecting means 59 and the other selecting means 70 will generally, though not necessarily, be of the same nature. The apparatus is equipped with means 71 for determining at least the weight of the primary fluid container 14 and/or of the auxiliary fluid container 64 and/or of the regional anticoagulant container 10 and/or of the collection container 62. In particular, said means 71 comprises weight sensors, for instance respective scales A, B, C, D and E (for example at least an independent sensor for each fluid bag associated to the machine). In particular, there will be at least four of said scales, each pair being independent from the other, and each one measuring the respective weight of a bag. It should then be pointed out that there is a control unit or CPU 12 active (at least) on the blood circuit 17 and in particular active on the pressure sensor 48 for reading pressure values, on the blood pump 21, on the gas exchanger 46, on the other pressure sensor 49, and on the device for detecting the presence of air bubbles 55 and on its respective safety valve 20. The control unit 12 has also to control the dialysis fluid circuit 32 and, in particular, shall be input with the data detected by the scales A, B, C, D and (possibly) E and, concerning the weight of the bag 14, and shall act on the pump 25, on the selecting means 59, on the pressure sensor 60, then on the dialysate pump 26 and shall eventually receive the data detected by the scale A whose function is to determine the weight of the collection container 62. The control unit 12 shall also act on the infusion line 63 checking the weight of the auxiliary container 64 (checked by the scale C) and will be able to control both the infusion pump 65 and the other selecting means 70. The control unit 12 shall also act on the anticoagulant line 51 detecting the weight of the anticoagulant fluid container 10 by means of the scale B and suitably controlling the anticoagulant pump 54 according to the treatments to be carried out as below detailed and explained. As apparent, a regional anticoagulation system is implemented in the apparatus 1 of FIG. 1 to provide anticoagulation restricted to the extracorporeal blood circuit 17. The regional anticoagulation system is described in detail in the respective description paragraph.

However, the apparatus of FIG. 1 may be alternatively (or additionally) provided with a systemic anticoagulation system, such as a syringe pump for injecting heparin downstream the blood pump 21. Indeed, the algorithm of embodiments the invention as described in the subsequent detailed description works both in CRRT treatment configurations with RCA and in CRRT treatment configurations with systemic (or no) anticoagulation without RCA.

The Regional Anticoagulation System

A regional anticoagulation system comprises a source of regional anticoagulant 10, e.g., a container or a bag containing at least a substance having an anticoagulant effect. For example, citrate, in the form of pure sodium citrate ($Na_3$citrate) or mixture of sodium citrate and citric acid are used for blood anticoagulation purpose. Alternatively pure citric acid may be used as anticoagulant. Indeed, citrate has a high affinity for calcium in creating complexes and several steps of the coagulation cascade are dependent on blood (ionized) calcium. A proper decrease of ionized calcium concentration in the presence of citrate inactivates the coagulation cascade. Normal plasma includes about 1.1 to 1.3 mmol/l of ionized calcium, 0.1-0.2 mmol/l of complexed calcium and 0.9 to 1.2 mmol/l of protein-bound calcium. In order to achieve proper anticoagulation effects, general guidelines are to adjust citrate amount/dose as to reach an ionized calcium concentration of 0.20 to 0.35 mmol/l in the extracorporeal blood circuit after citrate infusion. Plasma with citrate addition for anticoagulation purposes would include (as an average) about 0.3 mmol/l of ionized calcium, 1.8 mmol/l of complexed calcium (mainly $Ca_3citrate_2$) and 0.2 mmol/l of protein-bound calcium. During RCA, intensity of anticoagulation can be adjusted via the amount of infused citrate. Post-filtration unit ionized calcium concentration is commonly used as key parameter (target in the 0.20-0.35 mmol/l range) and is measured e.g., with blood gas analyzer. The regional anticoagulation system is arranged to deliver the regional anticoagulant at a delivery point 50 in the extracorporeal blood circuit 17. Citrate infusion is preferably administered close to an access end of the blood withdrawal line 6 to get full anticoagulation of the extracorporeal blood circuit 17. In general the delivery point 50 is located upstream the blood pump 21; however, it is not excluded that the delivery point 50 is located in the blood withdrawal line 6 downstream the blood pump. Alternatively, or in combination, the delivery point 50 for citrate may be the inlet of the filtration unit 2. In this latter configuration, the dialysis fluid contains citrate in an amount sufficient to achieve ionized calcium level around 0.25-0.35 mmol/l in blood circuit downstream the dialyzer. Citrate may be added to the treatment fluid flowing along the supply line 8 using a corresponding concentrate bag/container in case the dialysis fluid is on-line prepared as in current apparatuses for chronic treatment. Alternatively, particularly in case of CRRT apparatuses, the source 14 for dialysis fluid is a container/bag including the proper citrate concentration or content. Commercial citrate solutions are generally packed in respective plastic bags (sources 10) and can be split between physiologic and concentrated solutions. Physiologic citrate solutions are solutions having sodium concentration about 140 mmol/l, such as Baxter PrismoCitrate 10/2 (with 10 mmol/l Nacitrate and 2 mmol/l citric acid) and Baxter RegioCit 18/0 (with 18 mmol/l Nacitrate). Concentrated citrate solutions are for example, ACD-A (Anticoagulant Citrate Dextrose Solution) from Biomet: mix of sodium citrate (75 mmol/l), citric acid (38 mmol/l) and glucose; and Citrate 4% from Fresenius: citrate 136 mmol/l.

When citrate is infused into the blood withdrawal line 6 dose to the patient vascular access, blood pump speed is automatically adjusted as to take the operator set blood flow rate from access site (blood pump speed=$k*(Q_b+Q_{cit})$, wherein $Q_b$ is the set blood flow rate—desired at the access site and $Q_{cit}$ is the citrate infusion flow rate).

Citrate amount is prescribed through the 'Citrate Dose' parameter ($D_{citrate}$) which is the amount of citrate per liter of blood treated (mmol/l blood). Notably, citrate dose does not match with citrate concentration in the diluted blood reaching the filtration unit. The concept is rather to provide for an amount of citrate in proportion to the amount of calcium to be chelated. The set of the citrate pump 54 is:

$$Qcit = \frac{Dcitrate}{[citrate]_{PBP}} \times Qb$$

wherein
$Q_{cit}$ is the citrate infusion flow rate;
$Q_b$ is the set blood flow rate;
$D_{citrate}$ is the citrate dose; and $[citrate]_{PBP}$ is the citrate concentration in the anticoagulant source.

Citrate infusion is delivered with a dosage aimed to maintain ionized calcium level around 0.25-0.35 mmol/l in blood circuit downstream the dialyzer. Typically, citrate dose is included in the range 1.5 to 6.0 mmol/L-of-blood. The most common range is 2 to 4 mmol/L-of-blood. Citrate dose guideline of 3.0 mmol/L-of-blood is globally followed.

Ionized calcium and citrate complexes are rather small molecules which are easily transferred through the filtration unit 2. Loss rates are basically dependent on flow rates, filter efficiency with respect to small molecules and solute concentrations. While about half of the total calcium is not available to mass transfer during standard anticoagulation (since it is protein-bound), about 90% of total calcium becomes available during citrate anticoagulation. Therefore, citrate regional anticoagulation combined with the use of calcium free dialysis and/or replacement fluids implies significant calcium losses to dialysate. In extracorporeal blood treatments with RCA, calcium infusion is required to balance calcium losses to dialysate. During RCA, calcium infusion is adjusted to keep patient systemic ionized calcium in the normal range (e.g., 1.0-1.2 mmol/l). Therefore, the regional anticoagulation system of the apparatus 1 includes a source of ion balancing solution 11, which is reinfused in the blood, either in the return line 7, in particular close to the venous vascular access, or directly into the patient P (infusion into central catheter, which is recommended). The ion balancing solution 11, e.g., a syringe, a container or a bag, comprises a ion replacement infusion line 74 and a corresponding ion replacement pump 75 to drive delivery of a proper ion replacement infusion rate $Q_{ca}$. FIG. 1 shows a line 74 directly infusing into the patient P. Of course, line 74 may alternatively directly infuse in the blood return line 7, possibly close to the venous access. Notably, the auxiliary container 64 of FIG. 1 may (alternatively or in combination) be used for ion balancing in the blood return line 7. In the latter example, pre-infusion branch 67 remains dosed and unused to avoid calcium infusion upstream the filtration unit 2. In the example of FIG. 1, the syringe pump (not shown) usually used to deliver heparin may be alternatively used to deliver the ion balancing solution either directly into the patient or alternatively in the blood return line. The ion balancing solution includes ionized (concentrated) calcium and its infusion is performed to restore patient systemic ionized calcium at normal level. Notably, ion balancing solution may include also ionized magnesium and its infusion is performed to restore patient systemic ionized magnesium at normal level since also magnesium removal in dialysate is increased during RCA. The ion replacement infusion rate $Q_{ca}$ may be adjusted based on the revealed patient ionized calcium concentration in blood or an automatic control may be implemented, such as the one described in patent publication U.S. Pat. No. 8,668,825B2.

In an implementation, the ion balancing solution flow rate is kept proportional to the estimated calcium loss rate in dialysate. For example it is computed by the apparatus control unit through the equation:

$$Q_{ca} = \frac{CaComp \cdot J_{Ca}}{[Ca]} - \frac{Q_{rep} \cdot [[Ca]]_{rep}}{[Ca]}$$

Where CaComp is a calcium compensation parameter, $Q_{ca}$ is the ion balancing solution flow rate (ml/h), Jca is the estimated calcium loss rate in the dialysate (mmol/h), [Ca]

is calcium concentration of the ion balancing solution (mmol/l), $Q_{rep}$ is the replacement flow rate (ml/h), and $[Ca_{rep}]$ is calcium concentration of the replacement solution in post-dilution (mmol/l). Calcium compensation is the user-controllable setting, which might be set by the operator generally in a range between 5% and 200%.

Notably the above equation takes into account a post replacement solution including calcium. In case no calcium is in the post replacement solution (or no replacement solution is used) the second term of the equation should be disregarded (equal to zero).

Indeed, as to dialysis fluid (and replacement solution), they are generally calcium free to prevent transferring ionized calcium to blood. Moreover, the dialysis and/or replacement fluids have adapted buffer content due to citrate metabolism and adapted sodium if concentrated citrate solution (hypertonic) is used.

As to the buffer agent, since RCA has complex impact on acid-base balance equilibrium due to a significant fraction of citrate returned to patient (citrate is metabolized into bicarbonate), in the following section an analysis is made and risk control mitigation actions will be described in detail. Indeed, blood returned to the patient contains a significant concentration of citrate-calcium complexes. These complexes are (quickly) metabolized in liver, skeletal muscles, kidney releasing calcium in the blood stream, thus preventing systemic anticoagulation to develop; the citrate metabolism produces bicarbonate (3 moles $HCO_3^-$ for 1 mole citrate).

In this respect, the dialysis fluid may contain no buffer agent, e.g., no bicarbonate. A buffer agent from a source/container/bag 64 may be infused into the blood return line 7 via a suitable buffer agent supply line 63, 69, 66 and the corresponding buffer agent pump 65. Alternatively or in combination, to allow for acid-balance additional control, the apparatus 1 might also be designed to vary buffer balance of the extracorporeal blood circuit in an easy and controlled way via the possibility to set dialysis fluid (low) buffer concentration and/or to use source bags 14, 64 with different buffer concentration, e.g., in the range 15 to 25 mmol/l (and up to 40 mmol/l and/or down to 0 mmol/l) for bicarbonate.

As mentioned, citrate accumulation in the patient may correlate with hypocalcemia, metabolic acidosis (low bicarbonate production due to poor metabolism) or metabolic alkalosis (excessive bicarbonate production subsequent to high citrate load). As citrate measurement is not commonly available at the hospital, ratio of total calcium to ionized calcium is used as indicator, namely values below 2.5 are considered as normal (normal value below 2.0) and values above 2.5 indicate low ionized calcium concentration with respect to total calcium, possibly due to the presence of a significant systemic concentration of citrate. However, this monitoring is considered an insufficient measure, particularly in treatment involving relevant risks of acid/base unbalance, such as in RCA with 'large' flow rates, such as RCA+ECCO$_2$R, or certain SCUF treatments.

Additional risk control mitigations (RCM) below identified requires to be implemented, such as:
New alarm based on high citrate load, or more exactly net buffer load, applicable to all RCA prescriptions,
New prescription boundaries based on a second (higher) level of the same net buffer load parameter.
In the next sections, the implementation details of the two latter RCMs are further discussed.

Risk Control Mitigations

The risk control mitigations (RCMs) procedures specifically operate on the net buffer load monitoring. Control of net buffer load will be implemented in a generic way for all prescriptions in CRRT and particularly in respect to RCA and in respect to combined CRRT+ECCO$_2$R prescriptions. Though these new RCMs are not expected to be activated in the known and conventional CRRT prescriptions, this may not be true for the case of SCUF where they may (relevantly) warn about or prevent inadequate prescription (e.g., due to an excessive blood flow). The following embodiment consists in making available a parameter which characterizes the CRRT prescription (e.g., with RCA) with respect to acid-base (or buffer) balance. With this parameter, the prescriber gets a quantitative information on the intensity of the therapy with respect to the net patient buffer (bicarbonate) gain or loss. As mentioned, while this parameter is of special interest in the complex case of citrate anticoagulation, it remains also relevant to any extracorporeal dialysis therapy (run with systemic or no anticoagulation). Based on one or more predefined threshold (set by manufacturer or customized), the therapy system can trigger alerts in case the prescription matches with a risk of alkalosis (excessive buffer gain) or acidosis (insufficient buffer gain or net loss). Absolute limits preventing implementation of excessive prescriptions can also be considered.

Buffer Load Definition

Net buffer load during extracorporeal therapies ($J_{buffer\_load}$) is defined as the combination of (one or more of):
Bicarbonate generated from the metabolism of citrate infused to the patient ($J_{met\_cit}$) and/or of lactate infused to the patient ($J_{met\_lact}$)—more in general generated from metabolism of bicarbonate precursors,
Bicarbonate balance from the extracorporeal blood therapy ($J_{HCO3\_bal}$) which may match with net loss or net gain for the patient,
Acid infusion from e.g., citric acid content of the anticoagulant solution ($J_{H+}$), when relevant.

From the mathematical point of view, the general definition of net buffer load is:

$$J_{buffer\_load}=J_{met\_cit}+J_{HCO3_{bal}}(+J_{met\_lact})-J_{H+} \qquad (Eq.1)$$

By convention, net buffer load is positive in the case extracorporeal blood therapy provides for a net gain in buffer/bicarbonate to the patient, and negative in the case of loss in buffer.

From a physiologic perspective, the extracorporeal blood therapy is expected to provide for a net buffer gain to the patient, as to balance the metabolic production of protons (proteins metabolism). However, a net buffer loss may be desirable in the scenario where the patient initiates the therapy in the situation of (severe) metabolic alkalosis.

Buffer balance parameter is derived from a modelling of one or more of:
citrate infusion rate to patient (citrate load),
balance of bicarbonate and other buffers (e.g. lactate),
assumption on citrate metabolism (1 mole citrate metabolized in 3 moles of bicarbonate),
assumptions on patient systemic concentration for citrate, bicarbonate and other buffers (can be fixed values or computed from other sub-models).

Calculated buffer balance does not match with the current buffer balance of the CRRT running therapy (which would require specific knowledge of current patient levels for citrate and bicarbonate), but with the (normalized) Net Buffer Load expected at a steady state where patient bicarbonate would stabilize at e.g., 25 mM.

Acid-base steady state is established slowly and measurable changes are commonly present after 24 hours; two days appear as a reasonable minimum to consider that acid-base status is reaching steady state in the context of CRRT.

In the framework of the buffer balance analysis here introduced, acid-base balance steady state is reached when:
Patient systemic citrate concentration has stabilized across all the body compartments, thus leading to constant citrate load and bicarbonate generation,
Patient bicarbonate concentration has stabilized across all the body compartments as a result of Net Buffer Load balancing the metabolic proton generation rate $G_{H+}$.

Citrate Load

Citrate load is defined as the net infusion rate of citrate to the patient and it matches with the difference between the citrate infusion rate from the pre-blood-pump (PBP) circuit ($J_{cit\_PBP}$) and the citrate removal rate into dialysate ($J_{cit\_dial}$). See FIG. 2 citrate infusion in the blood circuit and citrate losses through dialyzer/dialysate.

From the mathematical point of view, the definition of patient citrate load is:

$$J_{citrate\_load} = J_{cit\_PBP} - J_{cit\_dial} \quad \text{(Eq.2)}$$

Computation of citrate infusion can be expressed in two ways, according to the definition of citrate dose ($D_{cit}$).

From the mathematical point of view, the definition of citrate infusion rate is:

$$J_{cit\_PBP} = Q_{cit} \cdot C_{cit_{PBP}} = D_{cit} \cdot Q_b \quad \text{(Eq.3)}$$

Citric acid and citrate forms are considered in the same way in this approach.

Removal rate of citrate into the dialysate is expressed from the definition of filter clearance for the citrate-calcium complexes ($K_{cit}$) and the citrate concentration (in plasma water) at the filter inlet. From the mathematical point of view, the definition of citrate removal to dialysate is:

$$J_{cit\_dial} = K_{cit} \cdot Cpw_{cit\_inlet} \quad \text{(Eq.4)}$$

Citrate Load (Main Variant)

The hypotheses for modelling the citrate mass transfer in the extracorporeal blood circuit includes the assumptions that citrate is distributed in plasma (and not in red blood cells), that CRRT filter citrate clearance is computed also based on citrate concentration in plasma water for mass transfer computations, that consideration is taken of patient citrate metabolism and non-zero steady state citrate concentration at blood access and that patient citrate clearance is proportional to body weight.

The definition of plasma water flow rate at filter inlet is the following:

$$Qpw_{inlet} = Qpw + Q_{cit} + Q_{rep\_pre} = Q_b \cdot (1 - Hct) \cdot Fp + Q_{cit} + Q_{rep\_pre} \quad \text{(Eq. 12)}$$

The equations (equations 13) for computation of citrate clearance in CRRT with non-zero dialysis fluid and filtration flow rates are as follows:

$$K_{cit} = \frac{(Qpw_{inlet} \cdot Q_d - f_{cit} \cdot (Qpw_{inlet} - SC_{cit} \cdot Q_{fil}) \cdot (Q_d + SC_{cit} \cdot Q_{fil}))}{(Q_d - f_{cit} \cdot (Qpw_{inlet} - SC_{cit} \cdot Q_{fil}))} \quad \text{(Eq. 13)}$$

$$f_{cit} = \left( \frac{Qpw_{inlet} - SC_{cit} \cdot Q_{fil}}{Qpw_{inlet}} \cdot \frac{Q_d + SC_{cit} \cdot Q_{fil}}{Q_d} \right)^{\frac{1}{\gamma_{cit}}}$$

$$\gamma_{cit} = e^{\left( \frac{SC_{cit} \cdot Q_{fil}}{\frac{S}{RT_{cit}}} \right)} - 1$$

It is noted that citrate mass transfer parameters used for computation of above removal rate are known and constant values depending on the selected dialyzer.

For example, the following table reports the values for some used Prismaflex sets:

| Prismaflex set | S/RT$_{cit}$ ml/h | SC$_{cit}$ |
|---|---|---|
| M100 | 7500 | 1.0 |

During an RCA treatment, citrate concentration at the blood access is never zero as some citrate accumulates in the patient. This accumulation should be taken into consideration to avoid bias of about 10% (in case of neglecting). It requires the knowledge of the citrate metabolism rate ($K_{cit\_met}$) in liver and muscles of the patient that can vary in a wide range and significantly biased the final estimation. However it could be relevant to consider a 'minimum' accumulation that occurs for a patient having a 'normal' citrate metabolism.

In this respect, patient citrate concentration is computed at steady state, assuming a typical metabolic clearance value of 700 ml/min (from literature). Although not described in literature, patient citrate clearance is assumed as proportional to body weight.

The expression of patient systemic citrate concentration at steady state is the following:

$$Cp_{cit\_pat} = \frac{J_{citrate\_load}}{K_{cit\_met}} \quad \text{(Eq. 14)}$$

According to the above, estimation of patient citrate metabolic clearance (ml/min) is:

$$K_{cit\_met} = 700 \cdot \frac{BW}{72} \quad \text{(Eq. 15)}$$

The expression of citrate plasma water concentration at filter inlet is as follows:

$$Qp \cdot CP_{cit_{pat}} + J_{cit_{PBP}} = Qpw_{inlet} \cdot Cpw_{cit\_inlet} \quad \text{(Eq.16)}$$

Combination of above Equation 2, Equation 4, Equation 14 and Equation 16 allows eliminating citrate concentration parameters and expressing patient citrate load as a function of flow rates and clearances.

$$J_{citrate\_load} = D_{cit} \cdot Q_b \cdot \left(1 - \frac{K_{cit}}{Qpw_{inlet}}\right) \cdot \left(1 - \frac{1}{1 + \frac{K_{cit\_met}}{K_{cit}} \cdot \frac{Qpw_{inlet}}{Qp}}\right) \quad \text{(Eq. 17)}$$

Citrate Load (Simplified Variant)

According to previously described main variant, the increase of patient systemic citrate concentration ($Cp_{cit\_pat}$) subsequent to citrate anticoagulation is considered and estimated through the equations 14 and 15. This choice leads to the above reported equation 17 for citrate load.

A simpler alternative to this formulation, is to neglect changes in the patient systemic citrate concentration and to take it as a constant, for example zero. Equation 14 and Equation 15 are consequently not used according to this alternative. In the case where patient citrate systemic concentration is assumed as zero ($Cp_{cit\_pat}=0$), Equation 16 and Equation 17 turn into following equations Equation 16' and Equation 17':

$$J_{cit\_PBP} = Qpw_{inlet} \times Cpw_{cit\_inlet} \quad \text{(Eq. 16')}$$

$$J_{citrate\_load} = D_{cit} \times Qb \times \left(1 - \frac{K_{cit}}{Qpw_{inlet}}\right) \quad \text{(Eq. 17')}$$

Bicarbonate Balance in Extracorporeal Blood Circuit

Figure 2:
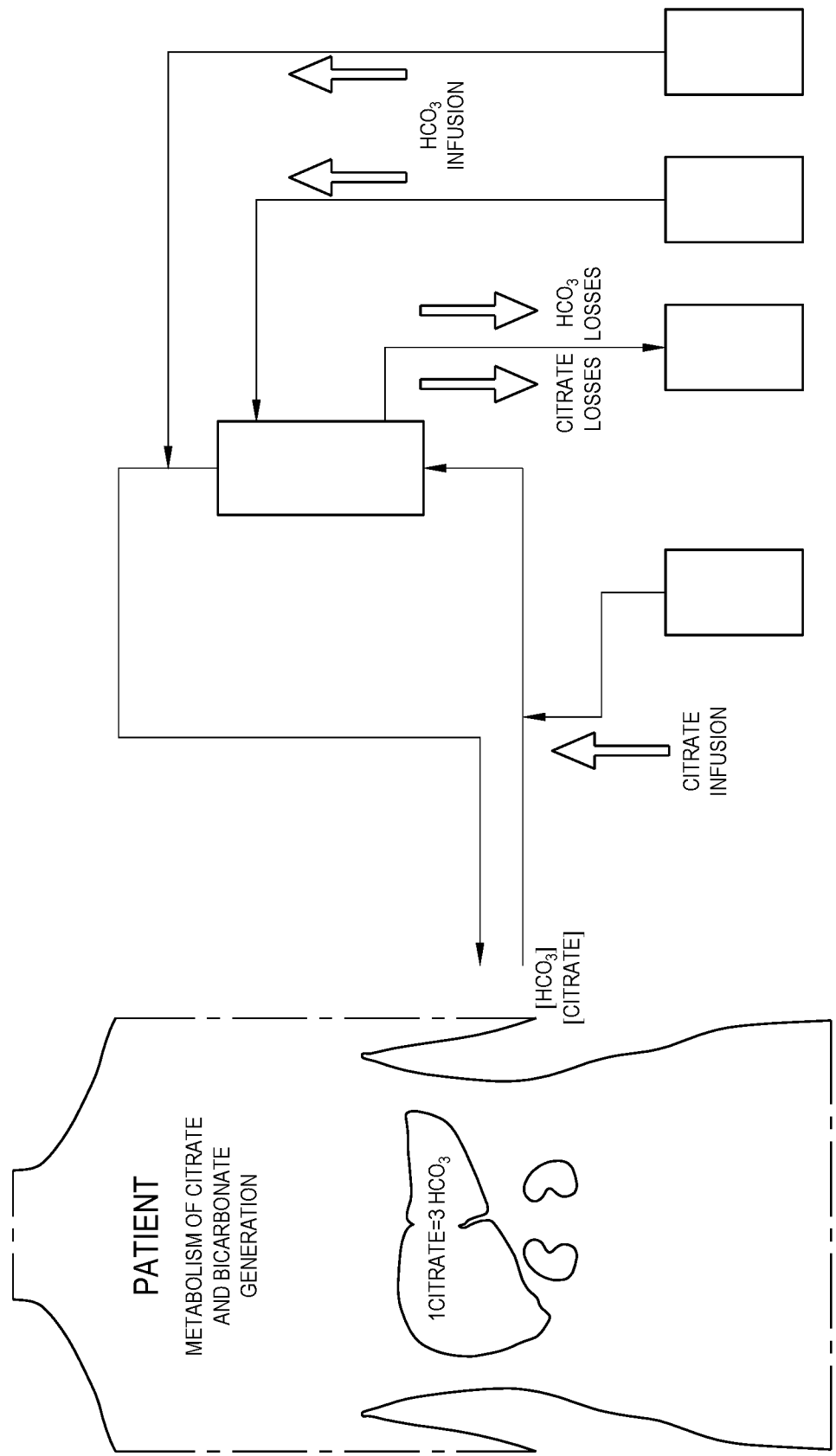
FIG. 2 schematically represents the mass transfer rates of interest during CRRT treatment with regional anticoagulation (RCA).

Bicarbonate balance is defined as the net infusion or loss rate of bicarbonate in the extracorporeal blood treatment; it matches with the difference between the infusion rate from the dialysis and/or replacement fluids ($J_{HCO3\_inf}$) and the bicarbonate removal rate into dialysate ($J_{HCO3\_dial}$); see FIG. 2.

The definition of bicarbonate balance rate is the following:

$$J_{HCO3\_bal} = J_{HCO3\_inf} - J_{HCO3\_dial} \quad \text{(Eq.5)}$$

The hypotheses for modelling the bicarbonate mass transfer in the extracorporeal blood circuit includes the assumptions that bicarbonate is distributed in plasma and red blood cells, that bicarbonate concentration at blood access $Cp_{HCO3\_pat}$ is fixed (e.g., equal to 25 mM); of course, a different (fixed) value for bicarbonate concentration at blood access may be used.

Other assumptions include that PBP citrate solution is bicarbonate free (in the reverse case, the bicarbonate content/concentration is to be taken into consideration in the bicarbonate balance), that CRRT filtration unit bicarbonate clearance is identical to urea clearance, and that bicarbonate removal in dialysate is computed according to similar equations as for citrate and consideration of bicarbonate concentration in plasma water for mass transfer computations.

Computation of bicarbonate infusion rate is based on knowledge of the fluids composition (i.e. known bicarbonate concentration).

$$J_{HCO3\_inf} = Q_d \cdot C_{HCO3\_d} + Q_{rep} \cdot C_{HCO3\_rep} \quad \text{(Eq.6)}$$

Fluid composition (i.e., bicarbonate concentration and/or replacement fluid prescription) may be entered by the physician (upon request from the dialysis apparatus) or read through e.g., a reader of the dialysis apparatus, for example by associating a product name with its bicarbonate content/concentration.

Equations of bicarbonate removal to dialysate are very similar to those of citrate; however, they differ for the fact that bicarbonate is present in the dialysis fluid, that the value of mass transfer parameter ($K_0A$) is different and that a fixed value is considered for patient systemic bicarbonate. Clearly, in case citrate was present in the dialysis fluid, the corresponding citrate load/balance may take into consideration such dialysis fluid citrate concentration in the corresponding equations for citrate and in the same way as below indicated for bicarbonate.

The definition of bicarbonate removal to dialysate is the following:

$$J_{HCO3\_dial} = Q_d \cdot C_{HCO3\_d} + K_{HCO3} \cdot (Cpw_{HCO3\_inlet} - C_{HCO3\_d}) + Q_{fil} \cdot C_{HCO3\_d} \quad \text{(Eq.7)}$$

Opposite to citrate, bicarbonate is easily transferred between red blood cells and plasma; whole blood water is thus considered for the computation of mass transfer to dialysate. Moreover, CRRT filter diffusive mass transfer coefficient of bicarbonate is taken identical to urea on the basis of their respective molecular weight (61 vs 60 g/mole). Sieving coefficient is taken as 1.

A constant physiological value of bicarbonate at blood access is considered.

The definition of blood water flow rate at filter inlet is as follows:

$$Qbw_{inlet} = Q_{bw} + Q_{cit} + Q_{rep\_pre} = Q_b \cdot [(1-Hct) \cdot Fp + Hct \cdot Frbc] + Q_{cit} + Q_{rep\_pre} \quad \text{(Eq. 18)}$$

The equations for computation of bicarbonate clearance in CRRT with non-zero dialysis fluid and filtration rates are similar to those for citrate; however, for the reasons above stated, mass transfer coefficients SC and $K_0A$ are different and the flow rate considered on the blood circuit is whole blood water flow (Qbw) instead of plasma water flow (Qpw).

The equations (equations 19) for computation of citrate clearance in CRRT with non-zero dialysis fluid and filtration rates are as follows:

$$K_{HCO3} = \frac{(Qbw_{inlet} \cdot Q_d - f_{HCO3} \cdot (Qbw_{inlet} - SC_{HCO3} \cdot Q_{fil}) \cdot (Q_d + SC_{HCO3} \cdot Q_{fil}))}{(Q_d - f_{HCO3} \cdot (Qbw_{inlet} - SC_{HCO3} \cdot Q_{fil}))} \quad \text{(Eq. 19)}$$

$$f_{HCO3} = \left(\frac{Qbw_{inlet} - SC_{HCO3} \cdot Q_{fil}}{Qbw_{inlet}} \cdot \frac{Q_d + SC_{HCO3} \cdot Q_{fil}}{Q_d}\right)^{\frac{1}{\gamma_{HCO3}}}$$

$$\gamma_{HCO3} = e^{\left(\frac{SC_{HCO3} \cdot Q_{fil}}{RT_{HCO3}}\right)} - 1$$

It is noted that bicarbonate mass transfer parameters used for computation of above removal rate are known and constant values depending on the selected dialyzer.

For example, the following table reports the values for some used Prismaflex sets:

| Prismaflex set | S/RT$_{bic}$ ml/h | SC$_{bic}$ |
|---|---|---|
| M100 | 17000 | 1.0 |

The plasma water concentration at filter inlet is derived from the set of below equations 20, namely:

$$Cpw_{HCO3\_pat} = \frac{Cp_{HCO3\_pat}}{Fp} \quad \text{(Eq. 20)}$$

$$Qbw \cdot Cpw_{HCO3_{pat}} + Q_{cit} \cdot 0 + Q_{rep\_pre} \cdot C_{HCO3\_rep} = Qbw_{inlet} \cdot Cpw_{HCO3\_inlet}$$

From above equations, the expression of bicarbonate plasma water concentration at filter inlet is:

$$Cpw_{HCO3\_inlet} = \frac{Q_{bw} \cdot \frac{Cp_{HCO3_{pat}}}{Fp} + Q_{rep\_pre} \cdot C_{HCO3\_rep}}{Qbw_{inlet}} \quad \text{(Eq. 21)}$$

Lactate Balance in Extracorporeal Blood Circuit (Optional)

Lactate balance is defined as the net infusion or loss rate of lactate in the extracorporeal blood treatment; it matches with the difference between the infusion rate from the dialysate and/or replacement fluids ($J_{lact\_inf}$) and the lactate removal rate into dialysate ($J_{lact\_dial}$).

Lactate can be used as an alternative buffer to bicarbonate with the benefit of getting more stable solutions. Lactate based dialysis fluid is well known in dialysis; for example, it is used in the home dialysis version of the System One device from NxStage. Furthermore, lactate is also present in a certain number of bicarbonate solutions in the form of lactic acid as to control pH and solution stability. This is the case for the Baxter Hemosol/PrismaSol CRRT solutions range having 3 mM lactic acid. Similarly to citrate, lactate is quickly metabolized into bicarbonate when infused to the patient, with a mole per mole conversion rate. Lactate may be modelled in the very same way as bicarbonate, assuming the patient steady state plasma lactate concentration is about 1.5 mM. Lactate clearance may be assumed identical to urea clearance, even though lactate molecular weight is about double of urea (112 vs 60 g/mole). However, clearance estimate error is minimal in the CRRT context where flow rates are the primary limiting factor. Of course, a more accurate estimate might be used, e.g. using the power dependence of $K_0A$ on solute molecular weight (meaning possible to derive $K_0A$_lactate from known $K_0A$ on Urea, creatinine, vitamin B12, inulin). The hypotheses for modelling of lactate mass transfer in the extracorporeal blood circuit include the assumptions that lactate is distributed in plasma and red blood cells and that CRRT filtration unit lactate clearance is identical to urea clearance. Further, patient steady state plasma lactate concentration at blood access is assumed fixed at 1.5 mM. Lactate mass balance in the extracorporeal blood circuit is computed with similar equations to bicarbonate considering metabolism of lactate load leading to 1 mole of bicarbonate per mole of lactate.

Mass transfer equations for lactate are as follows. The definition of lactate balance rate is the following:

$$J_{lact\_bal}=J_{lact\_inf}-J_{lact\_dial} \quad \text{(Eq.22)}$$

Computation of lactate infusion rate is based on knowledge of the fluid composition (i.e. known lactate concentration).

$$J_{lact\_inf}=Q_d \cdot C_{lact\_d}+Q_{rep} \cdot C_{lact\_rep} \quad \text{(Eq.23)}$$

Fluid composition (i.e., lactate concentration and/or replacement fluid prescription) may be entered by the physician or read through e.g., a reader of the dialysis apparatus.

The definition of lactate removal to dialysate is the following:

$$J_{lact\_dial}=Q_d \cdot C_{lact\_d}+K_{lact} \cdot (Cpw_{lact\_inlet}-C_{lact\_d})+ Q_{fil} \cdot C_{lact\_d} \quad \text{(Eq.24)}$$

Lactate is easily transferred between red blood cells and plasma; whole blood water is thus considered for the computation of mass transfer to dialysate. Moreover, CRRT filter diffusive mass transfer coefficient of bicarbonate is taken identical to urea. Sieving coefficient is taken as 1.

Lactate clearance ($K_{lact}$) is considered equal to bicarbonate clearance ($K_{HCO3}$) and therefore the control unit calculates it in the same way with same equations previously presented. The expression of lactate plasma water concentration at filter inlet is:

$$Cpw_{lact\_inlet} = \frac{Q_{bw} \cdot \frac{Cp_{lact\_pat}}{Fp} + Q_{rep\_pre} \cdot C_{lact\_rep}}{Qbw_{inlet}} \quad \text{(Eq. 25)}$$

Net Patient Buffer Load

In order to get net patient buffer load is necessary to obtain a relation between citrate infusion rate to patient (namely, citrate load) and bicarbonate generation. To achieve this target, the hypotheses on citrate metabolism include the following assumptions: metabolism of citrate load leads to 3 moles of bicarbonate per mole of citrate and Net Buffer Load (NBL) may be reduced by the rate of acid infusion, such as citric acid. The expression of bicarbonate generation rate from citrate metabolism (at steady state) is the following:

$$J_{met\_cit}=3 \cdot J_{cit\_load} \quad \text{(Eq.8)}$$

The expression referring to acid infusion rate is as follows:

$$J_{H+}=3 \cdot J_{citric\_acid}=3 \cdot Q_{cit} \cdot C_{citric\_pbp} \quad \text{(Eq.9)}$$

Combination of Equation 1, Equation 8 and Equation 9 leads to the expression for the net buffer load as a function of citrate load and bicarbonate balance:

$$J_{buffer\_load}=3 \cdot J_{cit\_load}+J_{HCO3\_bal}-3 \cdot J_{citric\_acid} \quad \text{(Eq.10)}$$

It is remarked that the expression of $J_{citrate\_load}$ is given in Equation 17, while full expression of $J_{HCO3\_bal}$ is to be derived from Equation 5, Equation 6, Equation 7, Equation 19 and Equation 21. From a therapy perspective, net buffer load should be positive as to neutralize the proton ($H^+$) generation rate $G_{H+}$ from metabolism. Literature report typical $G_{H+}$ values of about 1 mmol/day/kg, or 0.04 mmol/h/kg. Production of protons from metabolism is however strongly dependent on protein catabolism.

In case lactate is taken into consideration (optional), the expression for the net buffer load as a function of citrate load, lactate balance and bicarbonate balance becomes:

$$J_{buffer\_load}=3 \cdot J_{cit\_load}+J_{HCO3\_bal}+J_{lact\_bal}-3 \cdot J_{citric\_acid} \quad \text{(Eq.26)}$$

Prescription Boundaries

The control unit of the apparatus for extracorporeal blood treatment calculates and monitors a parameter ($J_{buffer\_load}$/BW) indicative of a steady state acid-base (or buffer) balance in the blood of the patient who has to undergo the CRRT blood treatment. With calculation, monitoring (and displaying) this parameter, prescriber gets a quantitative information on the intensity of the therapy with respect to the net patient buffer (bicarbonate) gain or loss. This parameter is of high interest in the complex cases of citrate anticoagulation and citrate anticoagulation combined with $ECCO_2R$, it remains also relevant to any extracorporeal dialysis therapy (run with systemic or no anticoagulation). In more detail, the control unit 12 determines the net buffer load, particularly at the apparatus setting (i.e., before the CRRT treatment is started). In even more detail, the control unit controls the normalized net buffer load (nNBL) as to prevent prescriptions likely to induce patient alkalosis and/or acidosis.

The definition of normalized net buffer load (nNBL) is the following:

$$nNBL = \frac{J_{buffer\_load}}{BW} \quad \text{(Eq. 11)}$$

nNBL is chosen as the indicative parameter of acid-base balance level at steady state, and is expressed as amount of buffer infused per unit of time and per patient kg (mmol/h/kg).

Review of published clinical data on CRRT with RCA at steady state has shown good correlation of this nNBL parameter with both steady state patient bicarbonate and base excess. Therefore, instead of using the (normalized) net buffer load as above defined, the buffer balance parameter could be expressed as the steady state bicarbonate concentration, once assuming a 'default' value for the normalized net buffer load (nNBL).

In the previously described embodiment, nNBL matches with the value of buffer balance when the patient reaches the assumed bicarbonate level (e.g; 25 mM)=>$nNBL_{25}$). If $nNBL_{25}$ matches with the protons generation rate (G), then steady state is reached and patient will stabilize at the assumed $HCO_3$ level (25 mM). Alternatively, if $nNBL_{25}$ is larger than the protons generation rate, patient bicarbonate will increase up to Ceq such as $nNBL_{ceq}$ matches with the (current) protons generation rate. In case $nNBL_{25}$ is lower than $G_{H+}$, then patient bicarbonate will stabilized at a lower value than the assumed level.

Variant with Steady State $HCO_3$ Indicator

Patient bicarbonate concentration ($Cp_{HCO3\_pat}$) could be taken as the indicative parameter of steady state acid-base equilibrium, providing that the (desirable/targeted) nNBL level has been chosen. In this scenario, previous equations may be re-arranged as to expressed patient steady state bicarbonate concentration as a function of a predefined nNBL level, for example nNBL0=0.1 mmol/h/kg. Citrate equations, namely equations 2-4, 12-17, 16' and 17', remain unchanged. Differently, bicarbonate equations require some rearrangement. In more detail, expression of steady state patient bicarbonate (rearrangement of Equation 20) is the following:

$$Cp_{HCO3\_pat} = \frac{Fp}{Qbw} \times \left(Cpw_{HCO3_{inlet}} \times Qbw_{inlet} - Q_{rep\_pre} \times C_{HCO3rep}\right) \quad \text{(Eq. 27)}$$

The expression of plasma water bicarbonate concentration at filter inlet (rearrangement of Equation 7) becomes:

$$Cpw_{HCO3\_inlet} = C_{HCO3\_d} + \frac{J_{HCO3\_dial} - Q_d \times C_{HCO3_d} - Q_{fil} \times C_{HCO3\_d}}{K_{HCO3}} \quad \text{(Eq. 28)}$$

The expression of bicarbonate losses to effluent (from equations 1 and 5):

$$J_{HCO3\_dial} = J_{HCO3\_inf} - J_{HCO3_{bal}} = J_{HCO3\_inf} + J_{met\_cit} - J_{H+} - J_{buffer\_load} \quad \text{(Eq.29)}$$

The relation between chosen/set nNBL0 and $J_{buffer\_load}$ is as follows:

$$J_{buffer\_load} = nNBL0 \times BW \quad \text{(Eq.30)}$$

$J_{buffer\_load}$ from equation 30, $J_{H+}$ equation 9, $J_{met\_cit}$ from equation 8 and equation 17 or 17' and $J_{HCO3\_inf}$ from equation 6 are input to equation 29; the latter is then combined with equation 28 so that all terms of the this combined expression are known. $Cpw_{HCO3\_inlet}$ is finally introduced in equation 27 to derive an expression of known/measured variables allowing the control unit 12 to determine the value of steady state patient bicarbonate which is the parameter to be controlled vs proper thresholds.

As apparent, this solution provides an alternative parameter, namely the steady state patient bicarbonate concentration (which is again a parameter indicative of the steady state acid-base balance in the blood of the patient who has to undergo to a CRRT blood treatment), with respect to the normalized buffer load parameter, allowing the control unit 12 to verify that a proper acid-base balance is maintained during the CRRT treatment.

Monitoring to Avoid Alkalosis

The normalized net buffer load is (optionally) monitored with respect to two different thresholds nNBL1 and nNBL2, namely a first level ($1^{st}$ threshold) that triggers an alert with reminders about a risk for metabolic alkalosis and a second level ($2^{nd}$ threshold) beyond which prescription becomes impossible. As a matter of fact, new RCMs should not generate unnecessary alerts in the context of the current daily CRRT-RCA prescriptions, while must prevent unsafe drifts.

In case following a prescription, the normalized net buffer load is included between the $1^{st}$ and the $2^{nd}$ nNBL thresholds (nNBL1<nNBL<nNBL2), a high buffer load alarm or alert is provided to the user. In this scenario, while prescription may be accepted, the control unit initiate two actions, namely the alert/alarm message is provided (e.g., displayed) to inform about the high citrate/buffer load and risk for patient alkalosis and a periodic anticoagulation checkpoint reminder of a sentence about the current prescription risk for alkalosis is provided so that the user is periodically reminded about the potential alkalosis issue. In case following a prescription, the normalized net buffer load is higher than the $2^{nd}$ nNBL threshold (nNBL>nNBL2), the control unit of the apparatus blocks settings in 'real time', by adding above criterion to the other prescription boundaries which already exist. In case, it is acceptable to manage this situation with an alarm (e.g., a message) indicating that the prescription is rejected due to an excessive buffer/citrate load. While the last (confirmed) settings are rejected, there may be a need to restore a valid prescription when dosing the alarm. Two potential alternatives (which the control unit may be configured to implement) are the following:

Option 1: restore previous (valid) prescription; or
Option 2: automatically move citrate dose (and/or blood flow rate) down to redefine a 'valid' prescription.

Threshold Values

Net buffer load quantifies the balance between citrate load matching with a buffer gain and buffer losses (primarily bicarbonate, secondarily lactate) associated to the CRRT process.

Although Net Buffer Load data is computed for the fixed patient bicarbonate level of 25 mM, actual buffer losses depend directly on the patient bicarbonate level. Qualitative aspects are:

Low bicarbonate losses, and higher actual buffer load, when patient bicarbonate is lower than 25 mM,
Higher bicarbonate losses, and lower actual buffer load, when patient bicarbonate increases beyond 25 mM.

At steady state, net buffer load is assumed to match patient needs for equilibrating net $H^+$ generation from metabolism. According to literature reference, typical H+ generation rate is about 1 mmol/day/kg, or 0.04 mmol/h/kg, and is strongly dependent on the catabolism of proteins. This means that, during CRRT, patient bicarbonate/acid-base balance is expected to stabilize at a point where net buffer load equals $H^+$ generation rate. An ideal RCA protocol could thus be defined as providing a normalized net buffer load of +0.04 mmol/h/kg in order to reach a 25 mM plasma bicarbonate at steady state. However, in the scenario of a hypercatabolic patient generating more than 1 mmol H+/day/kg, above protocol would stabilize the patient below 25 mM. Stabilization of this same patient at 25 mM bicarbonate would need a protocol associated to a net buffer load above +0.04 mmol/h/kg.

Due to limited intensity of the CRRT therapy, and although the expected exponential stabilization profile of acid-base balance over time, it might be considered to operate with a CRRT protocol matching with a rather 'alkalotic' steady state in order to quicker correct the common acidosis state present at therapy initiation (several papers report alkalosis developing after 2 or more days of therapy).

On the basis of literature analysis, assuming a target set for steady state patient bicarbonate concentration included between 24 and 26 mmol/l, in particular equal to 25 mmol/l, the first normalized net buffer load threshold should be between 0.25 and 0.35 mmol/h/kg. Particularly, the first threshold should be about 0.3 mmol/h/kg.

Normalized net buffer load values below 0.3 mmol/h/kg include all recommended protocols and most of reviewed RCA studies. This threshold matches with patient acid-base steady state values at the upper limit of 'normal' range according to observed correlation between nNBL and patient bicarbonate or base excess.

The second alarm threshold (nNBL2) is intended to block any prescription above this value. Selection of the proper value is thus more critical than for nNBL1 threshold. On the basis of literature alkalosis case reports and field data, the second normalized net buffer load threshold should be between 0.35 and 0.5 mmol/h/kg. Particularly, the second threshold should be about between 0.4 and 0.45 mmol/h/kg. Preferably, the selected value is about 0.4 mmol/h/kg.

At a normalized NBL of 0.40 mmol/h/kg, expected steady state for bicarbonate and base excess are respectively about 33 mM and +6.5 mM, which is already considered excessive. However, it could be considered that higher nNBL prescriptions are not at critical risks if applied for a limited time period, for example to quickly correct a strong acidosis state. For this reason, it may not be wise to set nNBL2 threshold too low.

Due to the limited 'intensity' of CRRT, and to the fact that development (or correction) of acid-base disorders takes time, typically more than 24 to 48 hours, it might be possible to allow high nNBL prescriptions (namely higher than nNBL2) over a short time period (e.g., few hours). The time period for allowing high nNBL (i.e., over the $2^{nd}$ threshold) prescriptions may be correlated to the difference between the normalized buffer load and the $2^{nd}$ threshold, the higher the distance the lower the allowable time.

Monitoring to Avoid Acidosis

The normalized NBL may also be monitored in order to avoid prescription possibly leading to metabolic acidosis.

In this situation, again one or two thresholds may be set to alert and/or to block a prescription. For example, a threshold may be set between 0 and −0.2 mmol/h/kg. Specifically, the threshold may be about −0.1 mmol/h/kg.

The invention claimed is:

1. A continuous renal replacement therapy (CRRT) apparatus comprising:
a filtration unit having a primary chamber and a secondary chamber separated by a semi-permeable membrane;
a blood circuit having a blood withdrawal line connected to an inlet of the primary chamber, and a blood return line connected to an outlet of the primary chamber, said blood circuit being configured for connection to a patient cardiovascular system;
a blood pump to circulate blood in the blood circuit;
a dialysis supply line connected to an inlet of the secondary chamber;
a dialysate line connected to an outlet of the secondary chamber;
one or more lines to transfer a respective solution into blood comprising an infusion line connecting for directly infusing into the blood a substitute solution including bicarbonate;
an infusion pump operating on the infusion line to deliver a replacement infusion rate;
a replacement solution bag connected to an end of the infusion line for infusing a solution including bicarbonate into blood;
at least one fluid source of a solution for each of said one or more lines, wherein said solution comprises at least one buffer agent in the form of bicarbonate or bicarbonate precursor;
a control unit configured to receive a patient prescription to set and deliver a CRRT blood treatment to the patient using the CRRT apparatus, the patient prescription including one or more of a blood flow rate in the blood circuit, a dialysis flow rate of dialysis fluid in the dialysis supply line, a patient fluid removal rate to be removed from the patient, wherein the control unit is further configured to calculate a steady state acid-base balance parameter in the blood of the patient who has to undergo a CRRT blood treatment, wherein said steady state acid-base balance parameter is calculated as a function of the concentration of said at least one buffer agent in said fluid source and as a function of the estimated or calculated patient systemic steady state concentration of bicarbonate and bicarbonate precursors;
wherein the control unit is configured to calculate the steady state acid-base balance parameter in the blood of the patient through a calculation of a bicarbonate balance from the CRRT blood treatment to be delivered in terms of an amount per unit of time, the calculation of the bicarbonate balance being a function of a replacement flow rate and bicarbonate concentration in the replacement solution;
wherein the control unit is further configured to calculate the steady state acid-base balance parameter in the blood of the patient as a function of one or more of:
an estimation of an amount per unit of time of bicarbonate generated from metabolism of the bicarbonate precursor infused to the patient;
a calculation of a lactate balance from the CRRT blood treatment to be delivered in terms of an amount per unit of time;
a calculation of an acid infusion from citric acid contained in the fluid source in terms of an amount per unit of time;
wherein the control unit is further configured to:
compare the steady state acid-base balance parameter in the blood of the patient with a threshold, and
generate an alert when the steady state acid-base balance parameter exceeds the threshold.

2. A continuous renal replacement therapy (CRRT) apparatus comprising:
a filtration unit having a primary chamber and a secondary chamber separated by a semi-permeable membrane;
a blood circuit having a blood withdrawal line connected to an inlet of the primary chamber, and a blood return line connected to an outlet of the primary chamber, said blood circuit being configured for connection to a patient cardiovascular system;
a blood pump to circulate blood in the blood circuit;
a dialysis supply line connected to an inlet the secondary chamber;

a dialysate line connected to an outlet of the secondary chamber;
one or more lines to transfer a respective solution into blood;
at least one fluid source of a solution for each of said one or more lines, wherein said solution comprises at least one buffer agent in the form of bicarbonate or bicarbonate precursor;
a control unit configured to receive a patient prescription to set and deliver a CRRT blood treatment to the patient using the CRRT apparatus, the patient prescription including one or more of a blood flow rate in the blood circuit, a dialysis flow rate of dialysis fluid in the dialysis supply line, a patient fluid removal rate to be removed from the patient,
wherein the control unit is further configured to:
calculate a steady state acid-base balance parameter in the blood of the patient who has to undergo a CRRT blood treatment, wherein said steady state acid-base balance parameter is the net buffer load or the normalized net buffer load, and is calculated as a function of the concentration of said buffer agent in said fluid source and as a function of the estimated or calculated patient systemic steady state concentration of bicarbonate and bicarbonate precursors,
calculate the steady state acid-base balance parameter in the blood of the patient as a function of one or more of:
an estimation of an amount per unit of time of bicarbonate generated from metabolism of the bicarbonate precursor infused to the patient,
a calculation of a lactate balance from the CRRT blood treatment to be delivered in terms of an amount per unit of time;
a calculation of an acid infusion from citric acid contained in the fluid source in terms of an amount per unit of time;
compare the steady state acid-base balance parameter in the blood of the patient with a threshold, and
generate an alert when the steady state acid-base balance parameter exceeds the threshold,
wherein the net buffer load during an extracorporeal blood treatment is the sum of bicarbonate generated into the patient from the metabolism of bicarbonate precursors, including citrate, and bicarbonate balance to the patient from the extracorporeal blood therapy.

3. A continuous renal replacement therapy (CRRT) apparatus comprising:
a filtration unit having a primary chamber and a secondary chamber separated by a semi-permeable membrane;
a blood circuit having a blood withdrawal line connected to an inlet of the primary chamber, and a blood return line connected to an outlet of the primary chamber, said blood circuit being configured for connection to a patient cardiovascular system;
a blood pump to circulate blood in the blood circuit;
a dialysis supply line connected to an inlet the secondary chamber;
a dialysate line connected to an outlet of the secondary chamber;
one or more lines to transfer a respective solution into blood;
at least one fluid source of a solution for each of said one or more lines, wherein said solution comprises at least one buffer agent in the form of bicarbonate or bicarbonate precursor;
a control unit configured to deliver a CRRT blood treatment to the patient using the CRRT apparatus, wherein, to deliver the CRRT blood treatment, the control unit is configured to:
receive a patient prescription including one or more of a blood flow rate in the blood circuit, a dialysis flow rate of dialysis fluid in the dialysis supply line, a patient fluid removal rate to be removed from the patient for setting a CRRT blood treatment,
calculate a steady state bicarbonate concentration in the blood of the patient who has to undergo the CRRT blood treatment, wherein said steady state bicarbonate concentration is calculated as a function of the concentration of said at least one buffer agent in said fluid source and as a function of one of the estimated or calculated net buffer load indicative of a steady state acid-base balance in the blood of the patient,
calculate the steady state bicarbonate concentration in the blood of the patient, and bicarbonate losses in the dialysate, further based on:
an estimation of an amount per unit of time of bicarbonate generated from metabolism of the bicarbonate precursor infused to the patient;
a bicarbonate infusion from the CRRT blood treatment to be delivered in terms of an amount per unit of time;
a predefined net buffer load chosen between 0 and 0.35 mmol/[h(kg)];
an acid infusion from citric acid contained in the fluid source in terms of an amount per unit of time;
compare the steady state bicarbonate concentration in the blood of the patient with a threshold, and
generate an alert when the steady state bicarbonate concentration in the blood of the patient exceeds the threshold.

4. The CRRT apparatus of claim 2, wherein said one or more lines for infusing a respective solution into blood comprises an infusion line for directly infusing into the blood a substitute solution including bicarbonate or bicarbonate precursor, the apparatus further comprising an infusion pump operating on the infusion line to deliver the substitute solution at a replacement infusion rate and a replacement solution bag connected to an end of the infusion line for infusing a solution including bicarbonate into blood.

5. The CRRT apparatus of claim 1, the infusion line is connected to the blood return line to post-infuse the solution including bicarbonate, the infusion line comprising a pre-infusion branch and a post-infusion branch to allow infusing both upstream and downstream the filtration unit.

6. The CRRT apparatus of claim 1, wherein said one or more lines for infusing a respective solution into blood comprises an anticoagulant line for directly infusing into the blood circuit an anticoagulant solution, the apparatus further comprising an anticoagulant pump operating on the anticoagulant line to deliver the anticoagulant solution at an anticoagulant infusion rate and an anticoagulant solution bag connected to an end of the anticoagulant line for infusing a solution including citrate into the blood circuit, wherein the anticoagulant line is connected to the blood withdrawal line.

7. The CRRT apparatus of claim 1, wherein the steady state acid-base balance parameter in the blood of the patient undergoing a CRRT treatment is a parameter function of a net buffer load in the patient expected at a steady state.

8. The CRRT apparatus of claim 1, wherein the steady state acid-base balance parameter in the blood of the patient undergoing a CRRT treatment is a parameter function of a normalized net buffer load in the patient expected at a steady state, wherein the net buffer load is normalized over a patient body weight.

9. The CRRT apparatus of the previous claim 7, wherein the control unit is configured to calculate the steady state acid-base balance parameter in the blood of the patient as follows:

$$nNBL = \frac{J_{buffer\_load}}{BW} = \frac{J_{met\_cit} + J_{HCO3\_bal} - J_{H+}}{BW}$$

alternatively, when also lactate balance is considered, the control unit is configured to calculate the steady state acid-base balance parameter in the blood of the patient as follows:

$$nNBL = \frac{J_{buffer\_load}}{BW} = \frac{J_{met\_cit} + J_{HCO3\_bal} + J_{met\_lact} - J_{H+}}{BW}$$

wherein:
nNBL is the steady state acid-base balance parameter,
$J_{buffer\_load}$ is a mass transfer rate of a net buffer during extracorporeal therapy,
$J_{met\_cit}$ is a mass transfer rate of bicarbonate generated from the metabolism of citrate infused to the patient,
$J_{HCO3bal}$ is a mass transfer rate of bicarbonate balance during extracorporeal therapy,
$J_{met\_lact}$ is a mass transfer rate of lactate infused to the patient,
$J_{H+}$ is a mass transfer rate of acid infusion, and
BW is a body weight of the patient.

10. The CRRT apparatus of claim 7, wherein the control unit is configured to calculate the steady state acid-base balance parameter during an extracorporeal blood treatment as the sum of bicarbonate generated from the metabolism of bicarbonate precursors, bicarbonate balance from the extracorporeal blood therapy, and acid infusion, if present.

11. The CRRT apparatus of the previous claim 10, wherein the bicarbonate precursors include at least one of citrate and lactate infused into the patient.

12. The CRRT apparatus of claim 10, wherein the bicarbonate balance from the extracorporeal blood therapy is a bicarbonate net loss or net gain for the patient.

13. The CRRT apparatus of claim 10, wherein the acid infusion comprises citric acid content.

14. The CRRT apparatus of claim 3, wherein the control unit is configured to calculate the steady state bicarbonate concentration parameter in the blood of the patient based on an estimation of an amount per unit of time of bicarbonate generated from metabolism of citrate infused to the patient, wherein the metabolism of citrate load leads to 3 moles of bicarbonate per mole of citrate at steady state, namely $$J_{met\_cit}=3 \cdot J_{cit\_load}.$$

15. The CRRT apparatus of claim 3, wherein the control unit is configured to calculate the steady state bicarbonate concentration in the blood of the patient imposing a constant value for the normalized net buffer load for the patient at steady state.

16. The CRRT apparatus of claim 3, wherein the control unit is configured to calculate the steady state bicarbonate concentration in the blood of the patient, and bicarbonate losses in the dialysate, based on a lactate balance from the CRRT blood treatment to be delivered in terms of an amount per unit of time.

17. The CRRT apparatus of claim 3, wherein the control unit is configured to calculate the steady state bicarbonate concentration in the blood of the patient, and bicarbonate losses in the dialysate, based on an algebraic sum of the estimation of bicarbonate form precursor metabolism, the bicarbonate infusion, the predefined net buffer load, and the acid infusion, the acid infusion being a negative term providing a loss in patient buffer.

18. The CRRT apparatus of claim 1, wherein the control unit is configured to calculate the steady state acid-base balance parameter in the blood of the patient based on an acid infusion contained in the fluid source in terms of an amount per unit of time, wherein the acid infusion is a function of an acid concentration and of an infusion rate of acid, the acid infusion being equal to 3 times the citric acid concentration multiplied by the infusion rate of citric acid.

19. The CRRT apparatus of claim 1, wherein the control unit is configured to calculate the steady state acid-base balance parameter in the blood of the patient based on an estimation of an amount per unit of time of bicarbonate generated from metabolism of citrate infused to the patient, wherein the metabolism of citrate load leads to 3 moles of bicarbonate per mole of citrate at steady state, namely $$J_{met\_cit}=3 \cdot J_{cit\_load}.$$

20. The CRRT apparatus of the previous claim 19, wherein the control unit is configured to calculate the citrate load as a function of patient citrate metabolic clearance, the metabolic clearance being based on a patient body weight.

21. The CRRT apparatus of the previous claim 19, wherein the control unit is configured to calculate the citrate load as a function of patient citrate metabolic clearance, the metabolic clearance being based on a patient body weight and being calculated as follows:

$$K_{cit\ met} = 700 \cdot \frac{BW}{72}$$

22. The CRRT apparatus of claim 19, wherein the control unit is configured to calculate the citrate load as a function of citrate clearance, the control unit being further configured to calculate the citrate clearance as a function of one or more flow rates, including one or more of dialysis flow rate, plasma water flow rate, ultrafiltration rate in filtration unit, and wherein the control unit is configured to calculate the citrate clearance as a function of the filtration unit intended for CRRT treatment.

23. The CRRT apparatus of claim 16, wherein the control unit is configured to calculate the citrate load as a function of one of:
citrate dose and blood flow, namely according to $D_{cit} \cdot Q_b$, or
citrate flow rate in an anticoagulant line and total citrate concentration,
namely according to $Q_{cit} \cdot C_{cit_{PBP}}$, wherein $Q_{cit}$ is the citrate flow rate and $C_{cit_{PBP}}$ is the total citrate concentration.

24. The CRRT apparatus of claim 16, wherein the control unit is configured to calculate the citrate load according to the following formula:

$$D_{cit} \cdot Q_b \cdot \left(1 - \frac{K_{cit}}{Qpw_{inlet}}\right) \cdot \left(1 - \frac{1}{1 + \frac{K_{cit\_met}}{K_{cit}} \cdot \frac{Qpw_{inlet}}{Qp}}\right)$$

or according to the following formula when patient systemic citrate concentration is assumed zero:

$$D_{cit} \cdot Qb \cdot \left(1 - \frac{K_{cit}}{Qpw_{inlet}}\right)$$

wherein:
- $D_{cit}$ is a citrate dose,
- $O_b$ is a blood flow rate,
- $K_{cit}$ is a filter clearance for the citrate-calcium complexes,
- $Opw_{inlet}$ is a plasma water flow rate,
- $K_{cit\_met}$ is a patient citrate metabolic clearance,
- $Op$ is a plasma flow rate.

25. The CRRT apparatus of claim 1, wherein the control unit is configured to calculate the steady state acid-base balance parameter in the blood of the patient based on a bicarbonate balance from the CRRT blood treatment to be delivered in terms of an amount per unit of time, wherein the bicarbonate balance is the difference between an infusion rate from the dialysis fluid and/or the replacement fluids and the bicarbonate removal into dialysate.

26. The CRRT apparatus of claim 25, wherein the control unit is configured to calculate the bicarbonate balance as a function of one or more of:
- the replacement flow rate and times the bicarbonate concentration in the replacement solution, namely as a function of $Q_{rep} \cdot C_{HCO3\_rep}$;
- a difference between bicarbonate plasma water concentration at filter inlet and bicarbonate concentration in the dialysis fluid;
- an ultrafiltration rate in filtration unit and bicarbonate concentration in the dialysis fluid;
- a bicarbonate clearance.

27. The CRRT apparatus of claim 26, wherein the control unit is configured to calculate the bicarbonate clearance as a function of one or more flow rates, dialysis flow rate, blood water flow rate, ultrafiltration rate in filtration unit, and wherein the control unit is configured to calculate the bicarbonate clearance as a function of the filtration unit intended for CRRT treatment.

28. The CRRT apparatus of claim 1, wherein the control unit is configured to compare the steady state acid-base balance parameter in the blood of the patient with a threshold, wherein either the threshold is an upper threshold; and the control unit is configured to generate an alert when the parameter is higher than the upper threshold, or the threshold is a lower threshold; and the control unit is configured to generate an alert when the parameter is lower than the lower threshold, wherein when the parameter exceeds the threshold, the control unit is configured to either issue the alert and keep an entered patient prescription, or to issue the alert and refuse the entered patient prescription,
wherein when the entered prescription is refused, the control unit is further configured to:
- restore a previous valid patient prescription; or
- automatically shift one or more parameters of the patient prescription, including a blood flow rate, and a citrate dose, to a proposed value defining a new valid patient prescription.

29. The CRRT apparatus of claim 28, wherein, a target set for steady state patient bicarbonate concentration comprises between 24 mmol/l and 26 mmol/l is set and the threshold includes an upper threshold comprised between 0.25 and 0.5 mmol/[h(kg)], wherein:
- a first upper threshold is comprised between 0.25 and 0.35 mmol/[h(kg)]; and/or
- a second upper threshold is comprised between 0.35 and 0.5 mmol/[h(kg)];

and wherein the threshold includes a lower threshold comprised between 0 and −0.2 mmol/[h(kg)], the control unit being further configured to issue and alert when the parameter is lower than the lower threshold.

30. The CRRT apparatus of claim 1, wherein the apparatus comprises:
- a source of dialysis fluid for providing fluid to the dialysis supply line, the dialysis fluid being free from a buffer agent;
- a replacement solution bag containing a substitute solution with a buffer agent, a buffer agent concentration in the substitute solution being comprised between 0 and 1000 mmol/l,
- said one or more lines for infusing a respective solution into blood comprises an infusion line connected to the replacement solution bag for infusing into the blood the substitute solution,
- wherein the infusion line is a post-infusion line infusing the buffer agent into the blood circuit downstream the filtration unit and the buffer agent comprising or being bicarbonate.

31. The CRRT apparatus of claim 1, wherein the control unit is configured to receive the patient prescription, and to calculate the steady state acid-base balance parameter in the blood of the patient based on one or more of the blood flow rate in the blood circuit, the dialysis flow rate of dialysis fluid in the dialysis supply line, and the patient fluid removal rate to be removed from the patient.

32. The CRRT apparatus of claim 31, wherein the control unit is configured to receive the patient prescription comprising:
- a fluid flow rate of a replacement fluid which is a total flow rate of replacement fluid infused pre- and post-filtration unit, and a pre- or -post infusion ratio of replacement fluid; or
- a post-infusion flow rate of a substitution fluid and/or a pre-infusion flow rate of a substitution fluid.

33. The CRRT apparatus of claim 2, wherein the control unit is configured to calculate the steady state acid-base balance parameter in the blood of the patient according to any one of the following definitions:

$$nNBL = \frac{J_{buffer\_load}}{BW} = \frac{J_{met\_cit} + J_{HCO3\_bal}}{BW}$$

or $$NBL = J_{buffer\_load} = J_{met\_cit} + J_{HCO3\_bal}$$

when acid infusion is considered, the control unit is configured to calculate the steady state acid-base balance parameter in the blood of the patient as follows:

$$nNBL = \frac{J_{buffer\_load}}{BW} = \frac{J_{met\_cit} + J_{HCO3\_bal} - J_{H+}}{BW}$$

or $$NBL = J_{buffer\_load} = J_{met\_cit} + J_{HCO3\_bal} - J_{H+}$$

when also lactate balance is considered, the control unit is configured to determine the steady state acid-base balance parameter in the blood of the patient as follows:

$$nNBL = \frac{J_{buffer\_load}}{BW} = \frac{J_{met\_cit} + J_{HCO3\_bal} - J_{met\_lact} - J_{H+}}{BW}$$

or $$nNBL = J_{buffer\_load} = J_{met\_cit} + J_{HCO3\_bal} + J_{HCO3\_lact} - J_{H+}$$

wherein:
- nNBL is the steady state acid-base balance parameter,
- $J_{buffer\_load}$ is a mass transfer rate of a net buffer during extracorporeal therapy,
- $J_{met\_cit}$ is a mass transfer rate of bicarbonate generated from the metabolism of citrate infused to the patient,
- $J_{HCO3bal}$ is a mass transfer rate of bicarbonate balance during extracorporeal therapy,
- $J_{met\_lact}$ is a mass transfer rate of lactate infused to the patient,
- $J_{H+}$ is a mass transfer rate of acid infusion, and
- BW is a body weight of the patient.

\* \* \* \* \*